United States Patent
Waterman et al.

(10) Patent No.: US 12,329,591 B2
(45) Date of Patent: Jun. 17, 2025

(54) WEIGHT DISTRIBUTION EXOSKELETON

(71) Applicant: StemRad Ltd., Tel Aviv (IL)

(72) Inventors: Gideon Waterman, Tel Aviv (IL); Tamar Fleisher, Tel Aviv (IL); Eyal Carmi, Ness Ziona (IL); Idan Zilzer, Tel Aviv (IL); Yoav Tikochinsky, Tel Aviv (IL); Nir Lilach, Kfar Yehoshua (IL); Amit Segal, Afula (IL)

(73) Assignee: StemRad Ltd., Tel Aviv (IL)

( * ) Notice: Subject to any disclaimer, the term of this patent is extended or adjusted under 35 U.S.C. 154(b) by 1516 days.

(21) Appl. No.: 16/685,572

(22) Filed: Nov. 15, 2019

(65) Prior Publication Data
US 2020/0155264 A1 May 21, 2020

Related U.S. Application Data

(60) Provisional application No. 62/767,664, filed on Nov. 15, 2018, provisional application No. 62/916,955, filed on Oct. 18, 2019.

(51) Int. Cl.
*A61F 5/01* (2006.01)
*A41D 13/00* (2006.01)
(Continued)

(52) U.S. Cl.
CPC .......... *A61B 90/60* (2016.02); *A41D 13/0002* (2013.01); *A61F 2/64* (2013.01);
(Continued)

(58) Field of Classification Search
CPC .................. A61F 5/0106; A61F 5/0123; A61F 2005/0146; A61F 2005/0158;
(Continued)

(56) References Cited

U.S. PATENT DOCUMENTS 4,599,998 A * 7/1986 Castillo ................ A61F 5/0123
74/109
4,655,201 A 4/1987 Pirmantgen
(Continued)

FOREIGN PATENT DOCUMENTS

| DE | 3609777 A1 | 9/1987 |
|---|---|---|
| WO | 2014138871 A1 | 9/2014 |
| WO | 2016210121 A1 | 12/2016 |

OTHER PUBLICATIONS

International Search Report issued in corresponding International Patent Application No. PCT/IB19/01242 dated Jun. 10, 2010.
(Continued)

*Primary Examiner* — Keri J Nelson
(74) *Attorney, Agent, or Firm* — Troutman Pepper Locke LLP

(57) ABSTRACT

A weight-distributing exoskeleton capable of supporting and/or control the distribution of at least part of the weight of a protective garment and/or face shield proximate the knee of the user. The exoskeleton may include a plurality of leg structures, each leg structure including a knee joint or knee hinge configured to bear the load of the protective garment, and a foot member including a magnetic quick release mechanism configured to control quickly engage with and release from the leg structures. The weight of the protective garment and/or face shield is transferred to the floor such that the user bears little to no burden of carrying it.

6 Claims, 20 Drawing Sheets

(51) Int. Cl.
*A61B 90/60* (2016.01)
*A61F 2/64* (2006.01)

(52) U.S. Cl.
CPC .......... *A61F 5/0106* (2013.01); *A61F 5/0123* (2013.01); *A61F 2005/0146* (2013.01); *A61F 2005/016* (2013.01)

(58) Field of Classification Search
CPC ... A61F 2005/016; A61F 5/013; A61H 1/024; A61H 1/0262
See application file for complete search history.

(56) References Cited

U.S. PATENT DOCUMENTS

| | | | |
|---|---|---|---|
| 6,953,442 B2 * | 10/2005 | Yamasaki | A61F 5/0123 602/22 |
| 9,808,073 B1 | 11/2017 | Maxwell et al. | |
| 2009/0014042 A1 | 1/2009 | Ashihara et al. | |
| 2015/0374513 A1 | 12/2015 | Ikeuchi | |
| 2018/0036159 A1 * | 2/2018 | Turrini | A61F 5/0123 |
| 2018/0296381 A1 | 10/2018 | Wayd | |

OTHER PUBLICATIONS

Partial Supplementary European Search Report issued in corresponding Application No. 19885282.4; mailed Oct. 11, 2022; 12 pages.

* cited by examiner

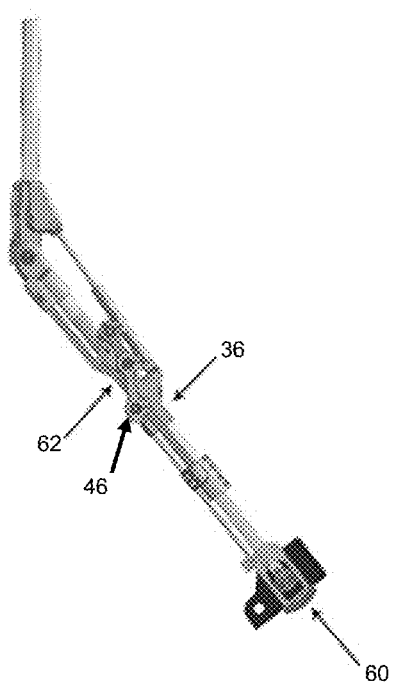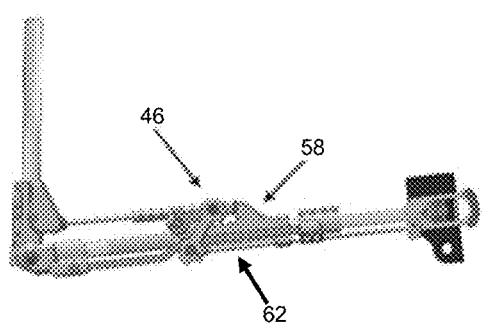
FIG. 5A  FIG. 5B
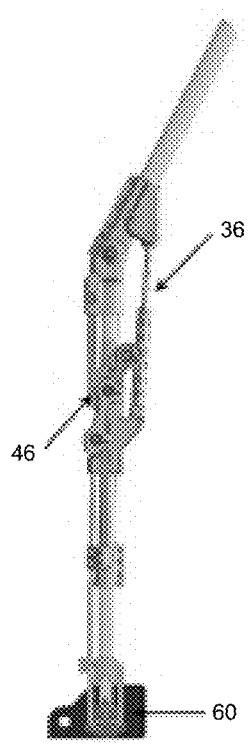
FIG. 5C

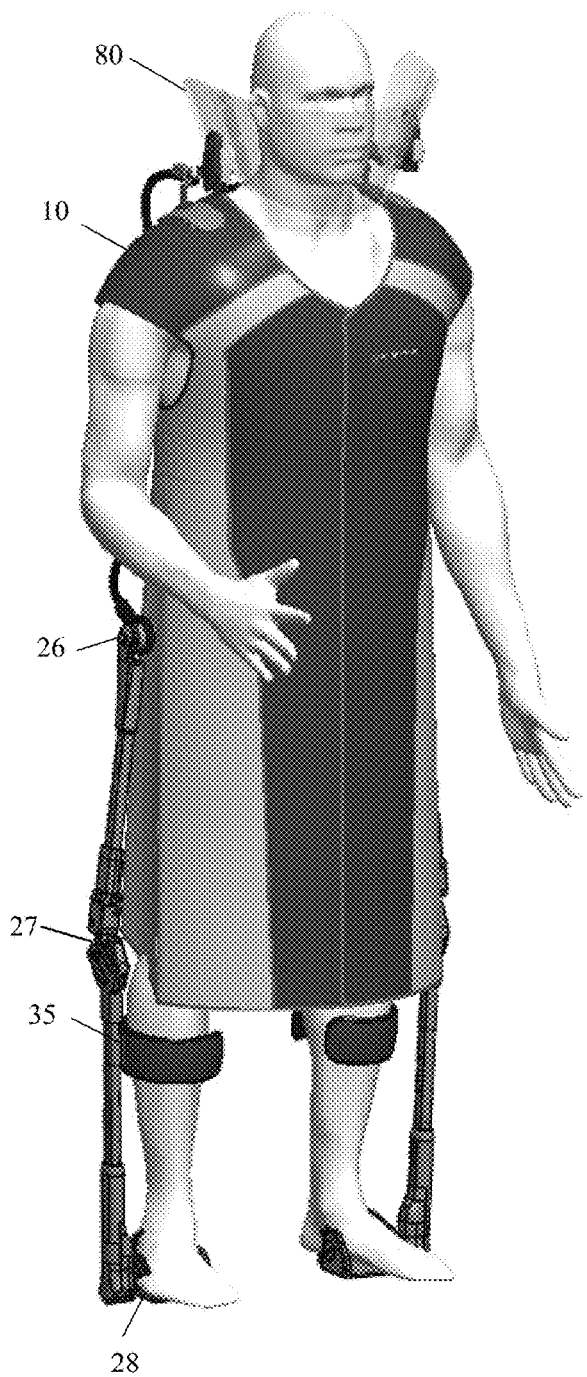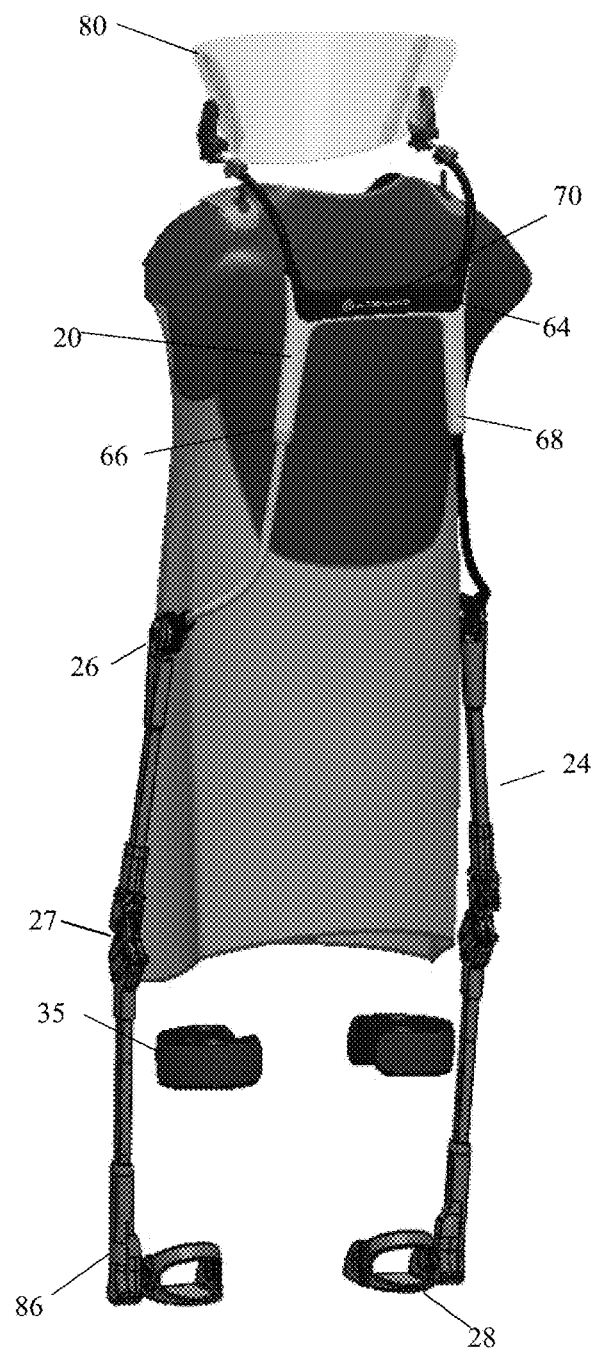
FIG. 12A
FIG. 12B

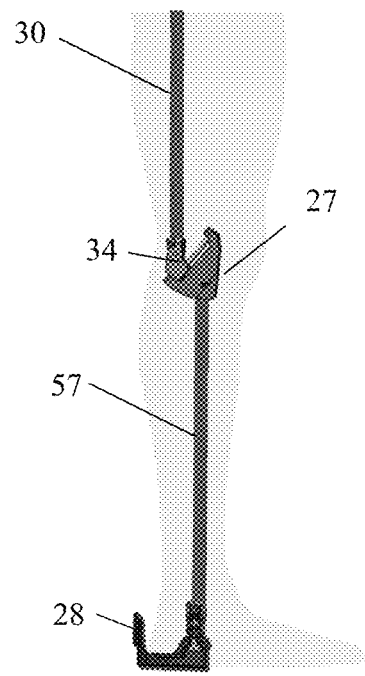
FIG. 13A
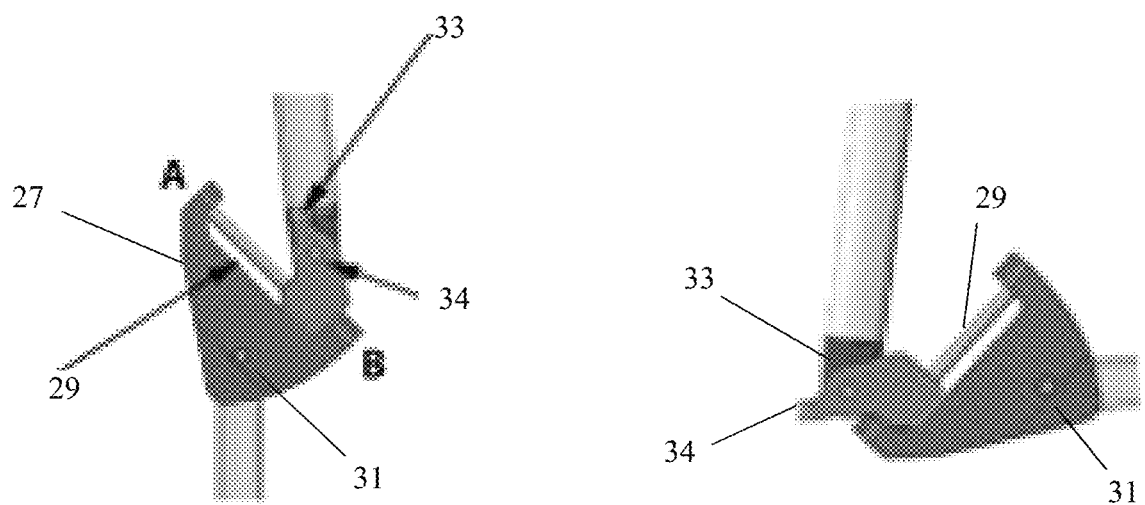
FIG. 13B
FIG. 13C

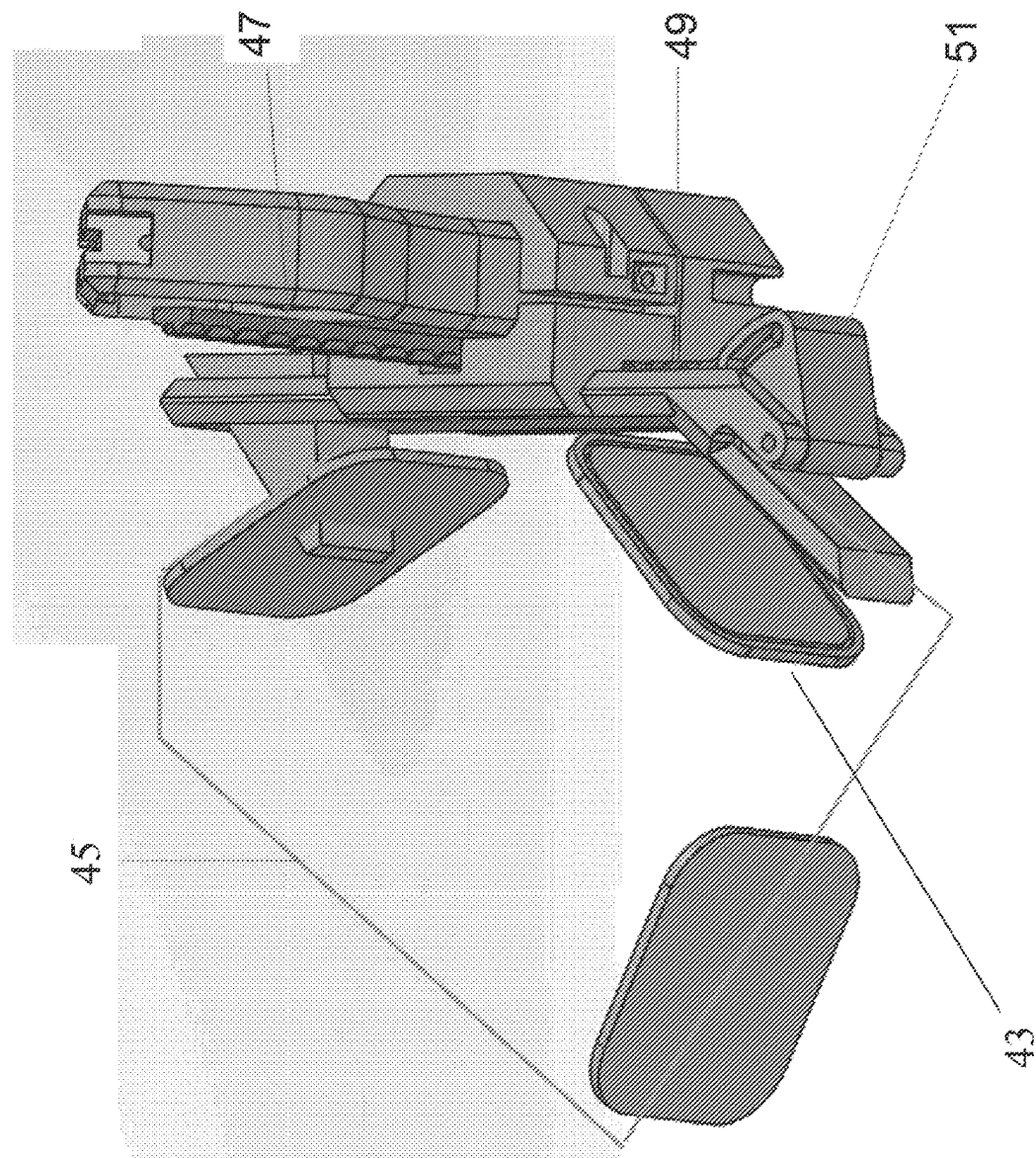

WEIGHT DISTRIBUTION EXOSKELETON

CROSS REFERENCE TO RELATED APPLICATIONS

This application claims priority to U.S. Provisional Application No. 62/767,664, filed Nov. 15, 2018 and U.S. Provisional Application No. 62/916,955, filed Oct. 18, 2019, the entire contents of which are hereby incorporated by reference.

FIELD OF INVENTION

The present invention generally relates to exoskeletal systems, and more particularly to weight-distribution exoskeletons that can generate a zero-gravity sensation for a wearer by offloading the weight of a load on the wearer.

BACKGROUND

Back, hip, and knee fatigue are common occupational injuries, which can decrease productivity and necessitate substantial medical expenses. Back, hip, and knee fatigue are often associated with occupations requiring frequent bending and lifting, each of which can levy considerable stress on the spine. While large loads increase the risk for injury, sustained static flexion of the spine while supporting the weight of the trunk alone can also lead to back pain as the extensor muscles of the lower back become fatigued. Similarly, prolonged awkward postures of the head and neck can produce discomfort.

During various treatment procedures, physicians are often required to adopt sustained static flexion of the spine. The performance of physicians in the operating room can be adversely affected by postural fatigue and discomfort, which are aggravated by the static postures frequently required during procedures. General surgeons, for example, can spend 65% of their operating time in static postures of the head and neck, with 14% of those in a flexed (forward bent) position. Physicians who perform minimally-invasive (e.g., laparoscopic, endoscopic, etc.) surgical procedures also experience long periods of static postures.

One subgroup of operating physicians that is believed to experience a higher-than-average incidence of back pain is interventionalists. These include neurosurgeons, radiologists, and cardiologists, for example, who operate using real-time radiography. The radiation levels in the operating room require the use of shielding garments (also called "leads") for the full duration of procedures. Some leads can weigh between 5-15 kg and the added weight of these garments on the trunk can potentially increase the risk for neck, shoulder, and/or back pain. One study showed that physicians who used shielding garments regularly (in this case, cardiologists who wore leads up to 8.5 hours per day) had the highest incidence of missed work days due to neck/back pain (21.3%) and required more treatment than other physicians who did not have to use shielding garments. The same study also showed a higher incidence of multiple-disc herniations of the cervical and lumbar spine among interventionalists. Approximately 20% of interventional cardiologists will develop symptoms of intervertebral disc degeneration, and about 5% will require surgical intervention to treat the condition, which typically requires 22 days or more of recovery. Moreover, because the activity of the lower back muscles is known to directly correlate with lumbar intervertebral disc pressure, prolonged exposure to high intervertebral pressures, such as when a shielding garment is worn, can lead to discomfort as well as permanent structural damage of the intervertebral discs.

Physicians often employ a variety of creative methods to try and mitigate discomfort, including the use of spinal orthotics worn under shielding garments and surgical gowns. Spinal orthotics such as soft belts and semi-rigid corsets that are currently available can achieve some degree of spinal offloading by increasing intraabdominal pressure as well as serving as a kinesthetic reminder to the wearer to prevent excessive flexion. These orthotics products are often designed to carry loads from the shielding garments on the posterior side of the body. However, it has been shown that the use of such commercially-available back belts provides no reduction in the likelihood of injury, as quantified through compensation claims and reported lower back pain. Custom-made orthoses produced by a trained orthotist have been shown to be more biomechanically effective than common mass-produced, non-customized, or over-the-counter models, but have several drawbacks: the individual manufacturing and fitting required are prohibitively expensive for common usage, the restricted maneuverability such orthoses create could be disadvantageous in the workplace, and the increased back postural muscle activity that some orthoses can produce could actually promote muscle fatigue.

There have been many products developed which purport to distribute the weight of protective garments. Mobile scaffolding is one such option and entails suspending the protective garment over its wearer. The scaffold must be wheeled around by two handles around the pelvis of the wearer. In another system, a protective garment along with a face shielding apparatus is suspended above the wearer by an overhead arm fixed to a ceiling. However, these systems have largely proved unsuccessful in the market as the burdens of the systems such as obtrusiveness in a treatment room, prohibition from certain ranges or types of motion or movement, and/or inordinate expense, outweigh the intended benefits.

Protective garments may also be used for chemical and radiation protection in non-medical circumstances such as nuclear leaks, chemical spills, etc. Providing a more mobile and low-profile shielding garment support could help facilitate such human contribution in those instances.

SUMMARY

Disclosed herein are various exemplary devices of the present invention that can address the above needs, the systems can be an exoskeleton that generally can include a load attachment mechanism, a plurality of leg structures, and a foot member. The exoskeleton can be joined to a load such as a protective garment and distribute the weight of the load through the exoskeleton to the floor.

In one example, a weight-distribution exoskeleton system can include a load, and an exoskeleton configured to engage the load having a plurality of leg structures, each leg structure with a pelvis joint, and a foot member configured to attach to a foot of a wearer of the load. The exoskeleton can provide a hanging force to counteract at least some weight of the load when an applied force from the load is encountered, the applied force from the load being at least partially transmitted to a floor through the foot member.

In another example, a weight-distribution exoskeleton system, with a load having a surface, and an exoskeleton configured to engage the surface of the load and having a plurality of leg structures. The exoskeleton may be configured to engage at least one of an outer surface and an inner surface of the load. Each leg structure can include a pelvis joint, and a foot member configured to attach to a foot of a wearer of the load. The exoskeleton can provide a hanging force to counteract at least some weight of the load when an applied force from the load is encountered. The applied force from the load is at least partially transmitted to a floor through the foot member.

In another example, a weight-distribution exoskeleton has a plurality of upper body attaching elements and a plurality of leg structures. Each leg structure includes a pelvis joint configured to attach the leg structure to an outer surface of a protective garment near a pelvis area of a wearer of the protective garment, and a foot member configured to attach to a foot of a wearer of the protective garment. At least one upper body attaching element provides a hanging force to counteract at least some weight of the protective garment when an applied force from the protective garment is encountered and the applied force from the protective garment being at least partially transmitted to a floor through the foot member.

In yet another example, a weight-distribution exoskeleton system can include a load and an exoskeleton configured to engage the load. The exoskeleton can include a plurality of leg structures and each leg structure can include a pivot joint proximate the pelvis of a wearer of the load, a knee rail mechanism proximate the knee of the wearer, a shin mechanism proximate the shin of the wearer, and a foot member configured to attach to a foot of the wearer. In some embodiments, the exoskeleton provides a hanging force to counteract at least some weight of the load when an applied force from the load is encountered, the applied force from the load being at least partially supported by the knee rail mechanism.

In an additional example, a weight-distribution exoskeleton system can include a load and an exoskeleton configured to engage the load. The exoskeleton can include a plurality of leg structures and each leg structure can include a pivot joint proximate the pelvis of a wearer of the load, a knee lever mechanism proximate the knee of the wearer, a shin mechanism proximate the shin of the wearer, and a foot member configured to attach to a foot of the wearer. In some embodiments, the exoskeleton provides a hanging force to counteract at least some weight of the load when an applied force from the load is encountered, the applied force from the load being at least partially supported by the knee lever mechanism.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 5A to 5C illustrate bending configurations of an exemplary leg structure of the present invention;

FIGS. 12A-12B illustrate configurations of another exemplary interaction of a load or protective garment and face shield with the exoskeleton of the present invention;

FIGS. 13A-13C illustrate configurations of another exemplary leg structure of the present invention;

FIG. 17 illustrates a configuration of an exemplary shin mechanism of the present invention.

DETAILED DESCRIPTION

Specific embodiments of the present invention are now described in detail with reference to the figures, wherein identical reference numbers indicate identical or functionality similar elements.

A weight-distributing exoskeleton as described herein can assist in offloading the weight of a protective garment, for example, from the body of a wearer of the garment. Preferably, the weight-distributing exoskeleton can offload the entire weight of a protective garment to help assuage the risk of back, hip, and knee injury and fatigue. The weight of a protective garment may be borne entirely by the exoskeleton and conveyed down to the floor. It is advantageous for the exoskeleton to attach to the body of a wearer and still permit adequate mobility. Embodiments of the weight-distributing exoskeleton may allow a wearer to rotate normally in place (e.g., turnabout), walk, and bend, flex (e.g. forwards and backwards) the trunk at the waist in one or more body planes. In a preferred embodiment, the weight-distributing exoskeleton is customized to a wearer's unique anthropometry. This customization may be facilitated by the use of easily-scalable computer aided design (CAD) models and three-dimensional (3D) printing of complex parts. In another embodiment, each exoskeleton may be tailored to fit multiple end wearers of a similar body type, so that a customer (e.g., a hospital) does not need to necessarily purchase a unique exoskeleton for each end wearer. The following detailed description is merely exemplary in nature and is not intended to limit the invention or the application and uses of the invention.

Figure 1A:
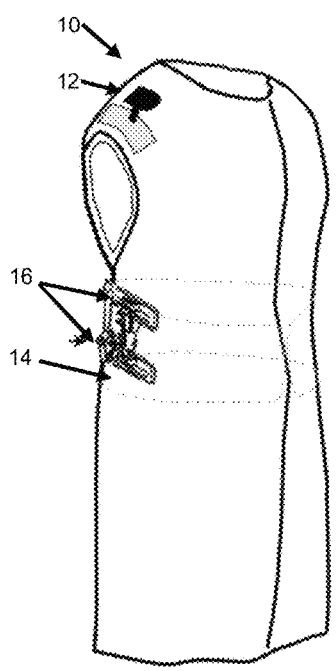
FIGS. 1A-1D illustrate configurations of an exemplary interaction of a load or protective garment with the exoskeleton of the present invention.
Figure 1B:
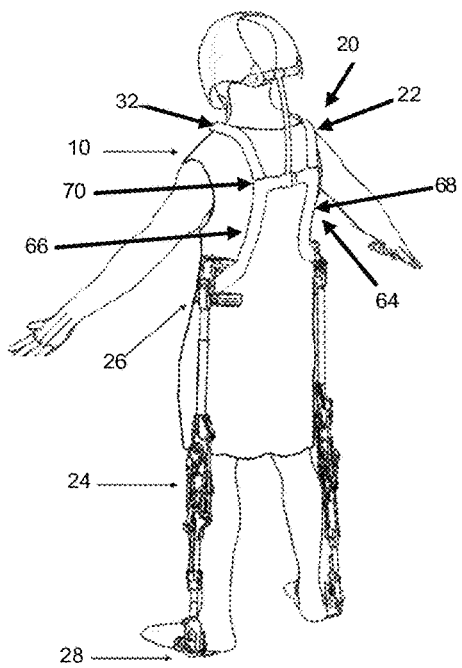

FIG. 1A shows a load such as a protective garment, and FIG. 1B shows the weight-distributing exoskeleton on a wearer of the protective garment. The illustrated exoskeleton is a passive orthosis, although it may be possible in some embodiments to include one or more active orthotic elements. This embodiment of the weight-distributing exoskeleton (20) hangs about the wearer's body. Such a compact design helps to avoid costly modifications to the operating room that are often required with prior art designs, such as arm-mounted shields that require the installation of overhead load-bearing arms or scaffolding. Additionally, the exoskeleton (20) has the potential to provide desired weight offloading without sacrificing any additional operating room volume, which nearly all prior art devices consume to at least some degree. Notably, unlike the orthotics products that carry loads on the posterior of the body, the weight of a load or protective garment may be borne by the exoskeleton (20) on an anterior side of the body of the wearer. As will be described in detail below, the weight-distributing exoskeleton 10 may be capable of transitioning between multiple settings, each setting allowing for a zero-gravity sensation for the wearer of a protective garment at differing body positions (e.g. walking, bending, leaning, sitting). Further, it should be understood that each setting can be at least partially transitional, so long as the exoskeleton can offload all or part of one or more applied forces. Accordingly, the exoskeleton can offload in multiple postures. For example, the exoskeleton may allow for a more natural bend in the knees while standing. The exoskeleton may also allow for a more natural bend in the knees during locomotion.

An example of an exoskeleton system, as illustrated in FIG. 1B can have an exoskeleton (20) configured to engage a load (10). The load (10) may be a personal protective equipment, including but not limited to protective garment, gears, helmets, googles, or other garments or equipment designed to protect the wearer's body from injury or infection. The hazards addressable by the load (10) may include physical, electrical, heat, chemicals, biohazards, and airborne particulate matter. The load (10) may be worn for job-related occupational safety and health purposes, as well as for sports and other recreational activities. Protective garment may be applied to traditional categories of clothing. Protective gear may be applied to items such as pads, guards, shields, and masks, among other possibilities.

The load (10) can include a surface. As will be described below, the exoskeleton is configured to engage the surface of the load. The exoskeleton may be configured to engage at least one of an outer surface and an inner surface of the load. The exoskeleton (20) can further include a plurality of leg structures (24). Each leg structure can include a pelvis joint (26), which may also be referred to as a pivot joint 26. Each leg structure can also include a foot member (28) and the foot member (28) can be configured to attach to a foot of a wearer of the load (10). In some embodiments, the foot member (28) can be a shoe holster. The exoskeleton (20) provides a hanging force to counteract at least some weight of the load (10) when an applied force from the load (10) is encountered. The leg structures can assist in supporting the hanging force when an applied force (e.g., weight) from a load or protective garment is encountered, thereby offloading some of the force from the wearer. The hanging force can be at least partially normal to an outer surface of the exoskeleton's components (e.g., in a direction away from the wearer), and is distinguishable from prior art devices that hold a protective garment above a wearer, or merely passively hold a protective garment around or adjacent to a wearer's body, for example. In a preferred embodiment, as shown in FIG. 1B the upper portion of the exoskeleton is designed to reside in back of or posteriorly to the wearer and the load or protective garment is supported by its hanging engagement with the exoskeleton and the distribution of its weight through the leg structures to the floor. In accordance with the disclosure, the applied force from the load (10) is at least partially transmitted to the floor through the foot member (28). In some instances, the weight of the load or protective garment is distributed down the exoskeleton (20) to the floor on the anterior side of the body of the wearer.

In one example, the exoskeleton (20) can further have a load attachment mechanism. In some embodiments, the load attachment mechanism can include a plurality of upper body attaching elements (22, 32) or the like. However, in some instances other fastening devices can be used to attach or assist in attaching the protective garment to a portion of the exoskeleton. The exoskeleton (20) can further include a plurality of leg structures (24). Other examples can have each leg structure with a pelvis joint (26) configured to attach the leg structure (24) to an outer surface of a protective garment (10) near a pelvis area of a wearer of the protective garment (10). In one example, each leg structure with the pelvis joint (26) may be configured to attach the leg structure (24) to an inner surface of the protective garment (10) near the pelvis area of the wearer of the protective garment (10). In exemplary embodiments, the plurality of upper body attaching elements (22, 32) can include a right shoulder attaching element (22) and a left shoulder attaching element (32). The exoskeleton (20) can also include a caudal member (64) that can connect the right shoulder attaching element (22) and the left shoulder attaching element (32) to the pelvis joints (26). The caudal member (64) can include a left beam (66) attaching the left shoulder attaching element (32) to the pelvis joint (26) of one of the leg structures and a right beam (68) attaching the right shoulder attaching element (22) to the pelvis joint (26) of another of the leg structure. The caudal member (64) can also include a central beam (70) extending between the left beam (66) and the right beam (68).

As shown in FIG. 1A, the load (10) can be a protective garment. The protective garment (10) may be custom-tailored, and it could be a single piece (e.g., a smock-like garment) or multiple pieces (e.g., a vest portion from the wearer's neck to the hips, with a skirt from the wearer's hips to knees or below). In another embodiment, the protective garment could be configured to be a part of or integrated with the exoskeleton. Additionally, other protective garment features may be included, such as a discrete vest, a neck collar for enhanced thyroid shielding, variable sleeve lengths, or a custom mass distribution (e.g., more mass toward the back to further reduce muscle strain in flexion by offloading torso weight and the weight of the protective garment). Further, smaller, larger, or differently shaped protective garments may be used. In some embodiments, the protective garment can be an ionizing radiation protective garment, an x-ray protective garment, a gamma protective garment, a ballistics protective garment, the garment can be configured to carry tools, combinations thereof, or the like. Still, in other embodiments, the load can be an assistive garment. For example, the load can be a tool belt.

The load or protective garment (10) can include a plurality of upper body receiving elements (12). In some embodiments, the plurality of upper body receiving elements (12) can be attached to a surface, such as an inner surface or an outer surface, of the load or protective garment (10). In further embodiments, the plurality of upper body receiving elements (12) can be attached to an upper surface of the protective garment (10). As shown in FIG. 1D, at least one of the upper body receiving elements includes a floating arc (11) attached to an inner area of the protective garment (10). Suitable floating arcs can be rigid or semi-rigid. A bridge component (13) can be attached to an outer area of the protective garment (10) above the floating arc (11). Additionally, a receiving component (15) formed with an orifice to receive an upper body attaching element (22, 32), can be attached to the bridge component via a ball joint (17). In some embodiments, the first ball joint (17) can include a quick release mechanism. In some embodiments, the ball joint (17) may be a composite, two-piece structure or a one-piece structure.

Figure 11:
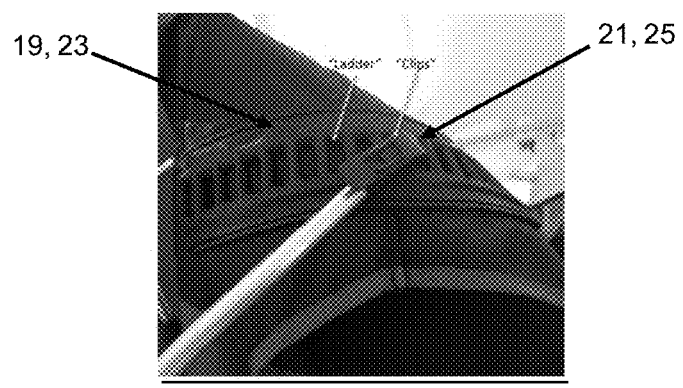
FIG. 11 illustrates a configuration of an exemplary ladder adjustment mechanism of the present invention.

As shown in FIG. 11, in other embodiments, the upper body receiving elements (12) may include a first ladder adjustment mechanism (19). The first ladder adjustment mechanism (19) can include a series of bars to permit adjustable attachment points for the upper body attaching element (22, 32). The first ladder adjustment mechanism (19) may further include a clips element (21) configured to securely engage an upper body attaching element (22, 32) to one of the bars. In some embodiments, the first ladder adjustment mechanism (19) is sewn or otherwise comparably attached to an outer area of the protective garment (10). It may be used as an attachment mechanism in lieu of the bridge component (13). Similarly, the clips element (21) may be used to securely engage an upper body attaching element (22, 32) in lieu of the ball joint (17) and receiving component (15). Moreover, any suitable mechanism may be used in lieu of the bridge component (13) or the first ladder adjustment mechanism (19) to secure the upper body attaching element (22, 32) to the protective garment or load (10).

The load (10) can further include a pelvic attachment belt (14). The pelvic attachment belt (14) can serve many purposes. First, it can be configured to stabilize the exoskeleton system on the wearer of the load. The belt (14) can also prevent mechanical stress, tension, and/or damage to the load or protective garment due to movement by the exoskeleton at the attachment points between the exoskeleton and the protective garment. Additionally, the belt (14) can fix the pelvic joint of the exoskeleton on the correct pelvic area to allow ergonomic movement. The pelvic attachment belt (14) also allows release of the garment from the exoskeleton such that when the wearer walks, it does not introduce uncomfortable shifts in the vertical axis. As will be appreciated, the pelvic attachment belt (14) can include padding, and can partially rest on a wearer's hips, or it may not rest on a wearer's hips at all. The belt (14) can also be disposed on an inner surface of the load or protective garment (10), or on an outer surface or an inner surface of the load or protective garment (10). Generally, the belt (14) will be disposed near the pelvic surface of the load or protective garment (10) but can be positioned near other areas of the wearer.

Figure 1C:
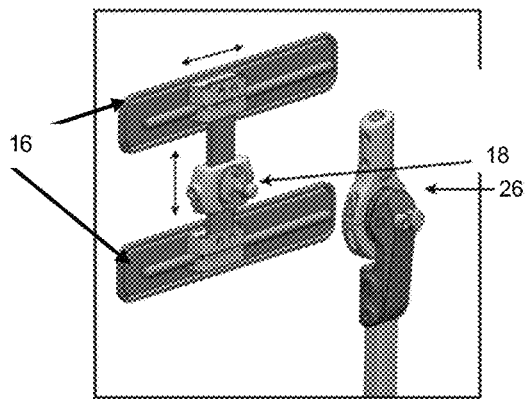
Figure 1D:
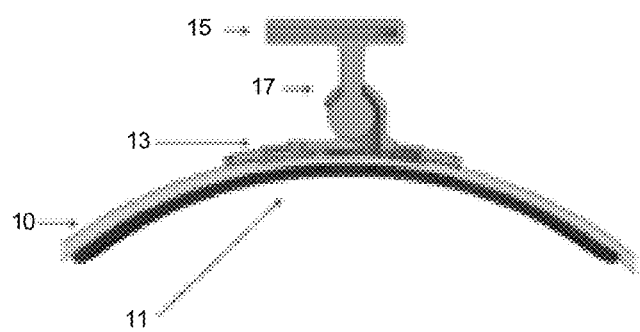

As shown in FIG. 1C, an example of the load (10) can include a plurality of pelvis rails (16). In some embodiments, at least one of the pelvis rails (16) can be mounted on an outer surface or an inner surface of the load or protective garment (10). In some embodiments, at least one of the pelvis rails (16) can be mounted on an outer, pelvic surface of the load or protective garment (10). In other embodiments, at least one of the pelvis rails (16) can be mounted on the pelvic attachment belt (14). Other examples have a lockable pelvis joint mechanism (18) which can be received by the pelvis rails (16). The lockable pelvis joint mechanism (18) can be slidably received by the pelvis rails (16). In some embodiments, the lockable pelvis joint mechanism (18) can be configured to permit sizing adjustments of the wearer. In some embodiments, the lockable pelvis joint mechanism (18) can be moved vertically on the pelvis rails (16) or horizontally along the rails to permit sizing adjustments of the wearer.

As shown in FIG. 11, in other embodiments, an example of the load (10) can include a plurality of second ladder adjustment mechanisms (23). The second ladder adjustment mechanism (23) can include a series of bars to permit adjustable attachment points for the lockable pelvis joint mechanism (18). The second ladder adjustment mechanism (23) may further include a clips element (25) configured to securely engage the lockable pelvis joint mechanism (18) to one of the bars. In some embodiments, the first ladder adjustment mechanism (19) is sewn or otherwise comparably attached to the protective garment (10) near the pelvis joint (26) and in lieu of the pelvis rails (16). Similarly, any suitable adjustment mechanism may be used in lieu of the pelvis rails (16) or the second ladder adjustment mechanisms (23).

Figure 2:
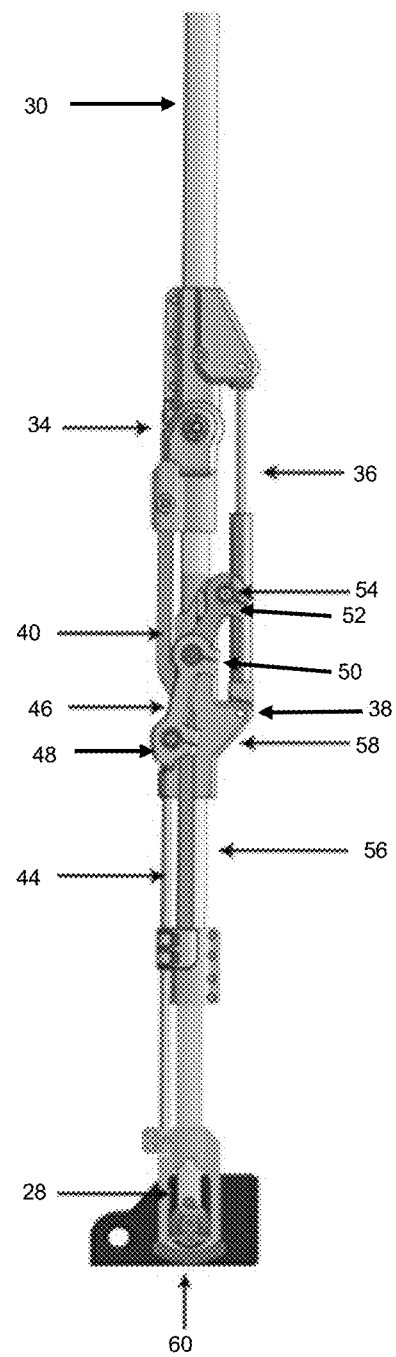
FIG. 2 illustrates a configuration of an exemplary leg structure of the present invention.

As shown in FIG. 2, each leg structure can further include a thigh beam (30). The thigh beam (30) can have one end attached to the pelvis joint (26). In some embodiments, a knee joint (34) can be attached to the thigh beam (30) on an end opposite of the pelvis joint (26). A resistive element (36) can be disposed posterior to the thigh beam (30) and have a bottom end (38). A threshold rail (40) can be disposed below and have one end attached to the knee joint (34). A pushing rail (44) can be disposed below the threshold rail (40). A collapsing hinge (46) can have a front attachment point (48), a middle attachment point (50), and a back attachment point (52). In some embodiments, the front attachment point (48) can be connected to the pushing rail (44). The back attachment point (52) can be connected to the resistive element (36). A collapse resistance spring (54) can be mounted on the collapsing hinge (46) near the back attachment point (52). In some embodiments, a calf rail (56) can be disposed substantially parallel and posterior to the pushing rail (44). The calf rail (56) can have one end connected to the thigh beam (30) at the knee joint (34) and an opposite end connected to the shoe holster (28). A resistive element slider (58) can be disposed on the calf rail (56). The resistive element slider (58) can be connected to the collapsing hinge (46) at the middle attachment point (50) and further attached to the bottom end of the resistive element (36). In some embodiments, the threshold rail (40) can be curved to extend downward between the calf rail (56) and the pushing rail (44).

Figure 3:
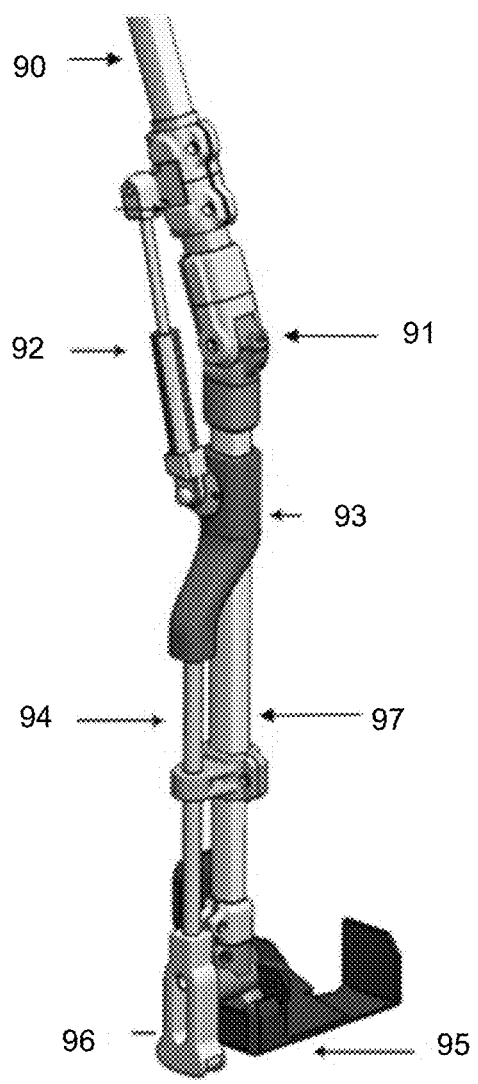
FIG. 3 illustrates a configuration of another exemplary leg structure of the present invention.

FIG. 3 shows an alternative leg structure for use with the exoskeleton. In this example, each leg structure can further include a thigh beam (90). The thigh beam (90) can have one end attached to the pelvis joint (26). A knee joint (91) can be attached to the thigh beam (90) on an end opposite of the pelvis joint (26). A resistive element (92) can be disposed posterior to the thigh beam (90). In some embodiments, the pushing rail (94) can be disposed below the resistive element (92) and parallel to calf rail (97). A resistive slider element (93) can be slidably received over the pushing rail (94) and the calf rail (97). As shown in FIG. 3, pushing rail (94) can include walking sensor (96), wherein the walking sensor (96) is adjacent the shoe holster (95). In some embodiments, walking sensors (60) and (96) can be mechanical sensors.

Figure 4:
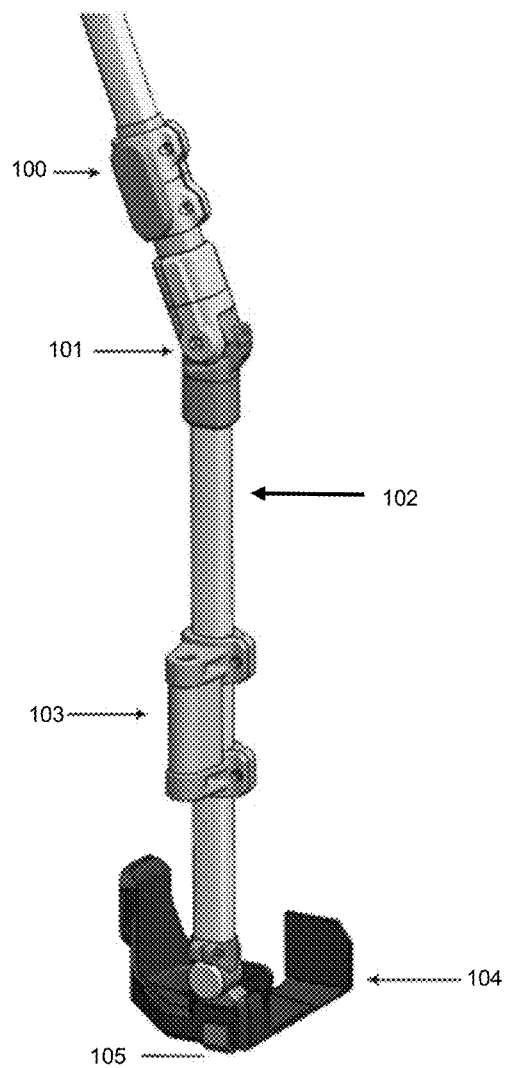
FIG. 4 illustrates a configuration of a further exemplary leg structure of the present invention.

FIG. 4 shows another alternative leg structure for use with the exoskeleton. In this example, each leg structure can include a knee joint (101), a calf rail (102), a motor (100), a battery holder (103), a shoe holster (104), and a walking sensor (105) disposed inside the shoe holster (104). The walking sensor (105) is connected to the motor (100) and the motor (100) locks and unlock the knee joint. In some embodiments, the sensor is an electronic sensor such as a pressure sensor, an optical sensor, micro switch, combinations thereof, or the like.

In use, when a wearer of the load or protective garment (10) is standing, the resistive element (36) can be configured to resist bending of the knee joint (34). This allows the load

(10) to be born through the thigh beam (90) and calf rail (97) and allow for limited movement without the knee joint (34) buckling and transferring weight to the wearer. In essence, the weight of the protective garment is distributed through the exoskeleton to the floor and the resistive element in turn holds the knee from bending. The resistive element can be a piston, spring, combinations thereof, or the like. As shown in FIG. 5A, the shoe holster (28) can include a walking sensor (60). When the leg of the wearer of the protective garment (10) is lifted to initiate or continue a walking position, the shoe holster moved up along with the foot. As the weight of the load or protective garment burdens the walking sensor, the walking sensor slides from inside the shoe holster (28) down to outside the shoe holster (28). Once the walking sensor (60) slides down to outside of the shoe holster (28), the pushing rail (44) is configured to be driven up towards the collapsing hinge (46), positioning the collapsing hinge (46) against the threshold rail (40) at a threshold point (62). The resistive element slider reacts by moving down the calf rail. This permits the resistive element to release its hold on the knee joint and prevent bending of the knee of the wearer. As shown in FIG. 5B, when the wearer's leg bends while walking, the collapsing hinge (46) is configured to move past the threshold point (62) and collapse. The resistive element slider reacts by moving further down the calf rail permitting further bending of a knee of a wearer without pushing against the piston. As shown in FIG. 5C, when the wearer's leg bends to initiate or continue sitting, the walking sensor (60) is configured to be locked in place by the floor. When the walking sensor (60) locks, the pushing rail (44) and the collapsing hinge (46) do not engage. The resistive element (36) then contracts and provides a supportive force to counteract at least some weight of the load or protective garment (10) when an applied force from the protective garment (10) is encountered.

Figures 6A, 6B:
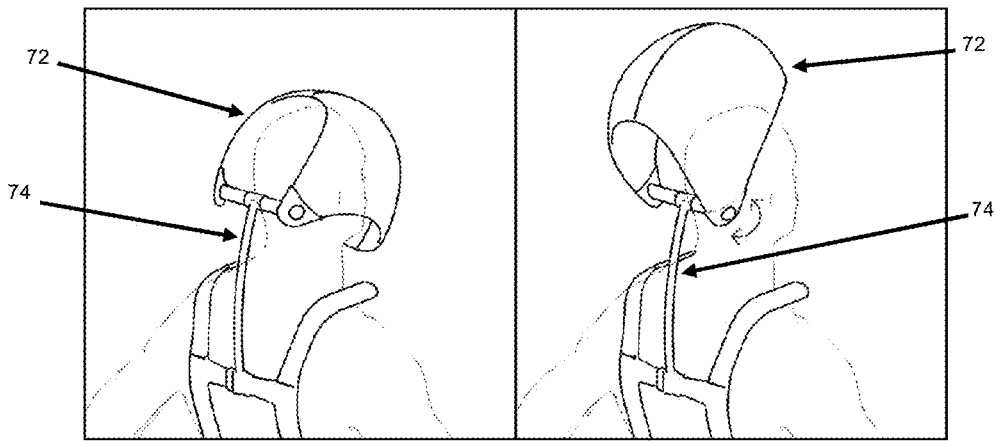
FIGS. 6A to 6B illustrate configurations of an exemplary face shield of the present invention.

The exoskeleton system can also incorporate support for protective gear for the face and head of the wearer. As shown in FIGS. 6A-6B, a static face shield (72) is attached to the caudal member (64). The face shield allows the head to move around inside the volume with good line of sight. In some embodiments, the static face shield (72) is attached to the caudal member (64) by at least one static balancing rod (74), at least one shoulder attaching element (22, 32), or a combination thereof. In other embodiments, the static face shield (72) is attached to the caudal member (64) by multiple static balancing rods.

Figure 7:
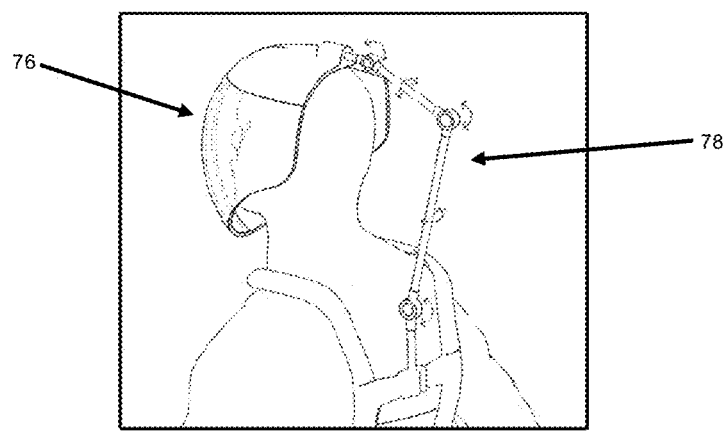
FIG. 7 illustrates configurations of another exemplary face shield of the present invention.

As shown in FIG. 7, a visor face shield (76) can be attached to the caudal member (64) by at least one resistive balancing rod (78), at least one shoulder attaching element (22, 32), or a combination thereof. The visor face shield is attached to the caudal member of the exoskeleton such that the weight of the shield is not imposed on the wearer, but instead imposed on the exoskeleton which distributes the weight to the floor while allowing freedom of movement (e.g. of the face and head) to the wearer. The wearer's movements guide the balancing rod to move along with and parallel to the wearer's movement. In some embodiments, the resistive balancing rods (78) can include at least one of a tension spring, a compression spring, a motion sensitive control, combinations thereof, or the like. Other examples include the visor face shield (76) attached to the caudal member (64) by multiple resistive balancing rod(s) (78). In some embodiments, the second balancing rod (78) can be configured to distribute the weight of the visor face shield (76) through the exoskeleton (20) and to the floor while permitting freedom of movement of a face and a head of the wearer.

Figures 8A, 8B, 8C:
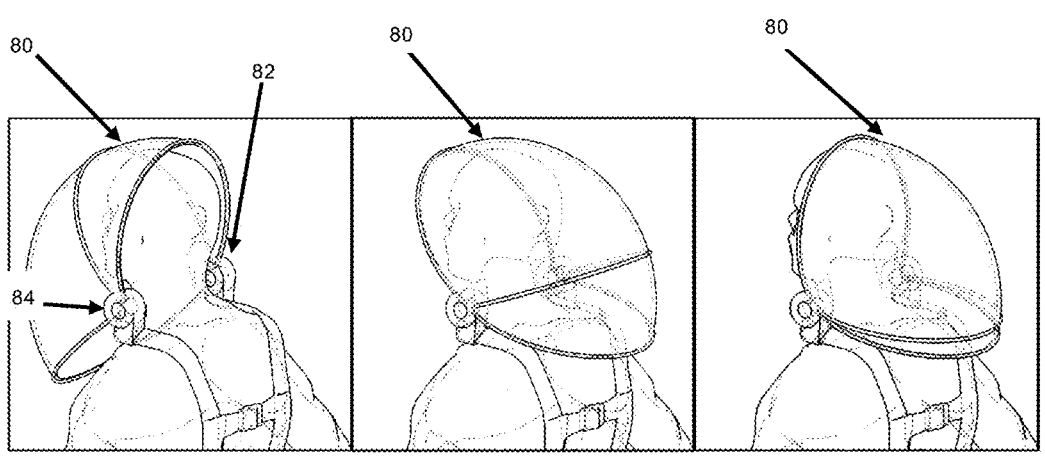
FIG. 8A to 8C configurations of a further exemplary face shield of the present invention.

As shown in FIGS. 8A-8C, a semi-rigid face shield (80) is mounted to the exoskeleton (20). The face shield (80) can be a two-piece structure such that a portion of the shield (80) can be lifted to expose the wearer's face but continue to cover the wearer's head. Similarly, a portion of the shield (80) can be lifted to expose the wearer's head but continue to cover the wearer's face. The semi-rigid face shield (80) can be mounted to the right shoulder attaching element (22). In some embodiments, the semi-rigid face shield (80) can be mounted to the right shoulder attaching element (22) by a right rotational joint (82). The semi-rigid face shield (80) can be mounted to the left shoulder attaching element (32). In some embodiments, the semi-rigid face shield (80) can be mounted to the left shoulder attaching element (32) by a left rotational joint (84). In use, the semi-rigid face shield (80) can be mounted such that the weight of the semi-rigid face shield (80) is distributed through the exoskeleton (20) and to the floor while permitting freedom of movement of a face and a head of the wearer.

Figure 9:
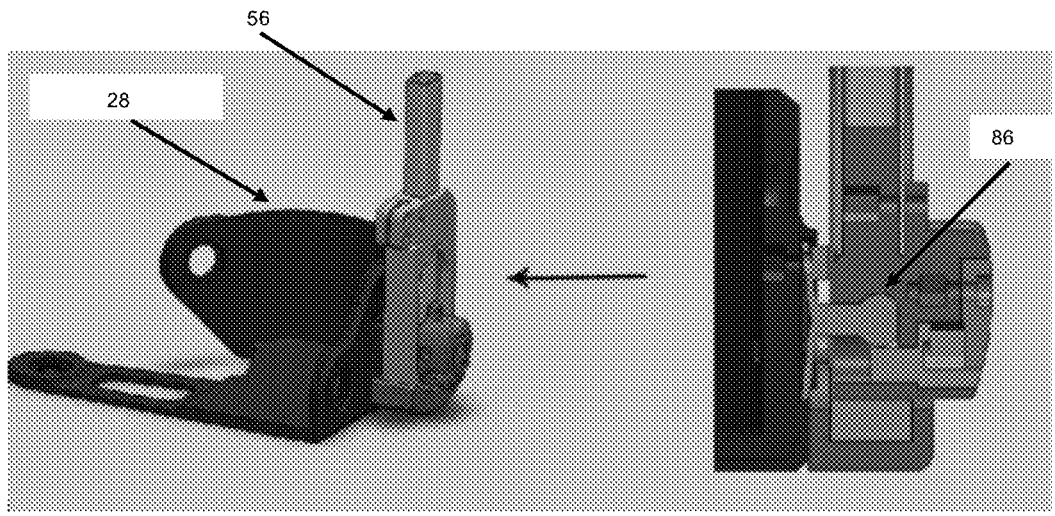
FIG. 9 illustrates configurations of an exemplary foot joint mechanism of the present invention.
Figure 10:
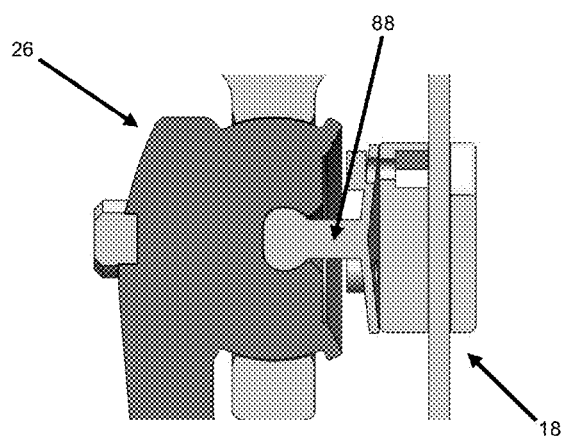
FIG. 10 illustrates configurations of an exemplary pelvis joint mechanism of the present invention.

As shown in FIG. 9, the shoe holster (28) is attached to the calf rail (56) by a first modified ball joint (86). In the examples illustrated in FIG. 10, the pelvis joint (26) is attached to the lockable pelvis joint mechanism (18) by a second modified ball joint (88). In some embodiments, the first modified ball joint (86) includes a quick release mechanism. The quick release mechanism permits the first modified ball joint (86) to move between a first position where it is engaged with a portion of the leg structure (e.g. near a wearer's ankle) to a second position where it is disengaged from the leg structure. In some embodiments, the second modified ball joint (88) similarly includes a quick release mechanism. In this example, the quick release mechanism permits the second modified ball joint (88) to move between a first position where it is engaged with a portion of the leg structure (e.g. near a wearer's hip) to a second position where it is disengaged from the leg structure.

In another embodiment, as shown in FIG. 12B, the load or protective garment is supported by its hanging engagement with the exoskeleton and the distribution of its weight through the leg structures and supported proximate the knee of the wearer. In accordance with the disclosure, the applied force from the load (10) is at least partially supported by knee rail mechanism (27). In some instances, the applied force from the load (10) is at least partially supported by knee lever mechanism (41).

With reference to FIG. 12A, the load (10) can further include a shin mechanism (35) proximate the shin of the wearer. The shin mechanism (35) can serve many purposes. For example, it can be configured to stabilize the exoskeleton system on the wearer of the load. Shin mechanism (35), as illustrated in FIG. 17 can include a shin cuff member (43) at least partially surrounding a shin of the wearer and a shin strap (45) configured to hold the shin cuff member (43) onto the shin of the wearer. Shin mechanism (35) can further include vertical teeth component (47), a horizontal teeth component (49), a release hook (51), and a quick release cable (53) connected to the vertical teeth component (47). In some embodiments, horizontal teeth component (49) and the vertical teeth component (47) can be configured to engage. In some embodiments, release hook (51) can be configured to hold the horizontal teeth component (49) and the vertical teeth component (47) in engagement, securing the shin strap (45) and shin cuff member (43) on the shin of the wearer. In some embodiments, quick release cable (53) can be configured to pull the vertical teeth component (47), thereby causing the horizontal teeth component (49) to move and disengage the shin strap (45), releasing the shin cuff member (43) from the shin of the wearer. Shin mechanism (35) can also prevent mechanical stress, tension, and/or damage to the load or protective garment due to movement by the exoskeleton proximate the knee of the wearer. As will be appreciated, the shin mechanism (35) can include padding, and may partially rest on a wearer's shins.

In another embodiment, as shown in FIGS. 13A-13C, the knee joint (34) can engage a knee rail mechanism (27) including knee rail (29) and attachment point (31). In some embodiments, the knee joint (34) is disposed on the knee rail (29) of the knee rail mechanism (27). In some embodiments, the knee joint slidingly engages the knee rail (29) on an end opposite attachment point. The knee joint (34) can also rotate about the knee rail (29) to allow for lateral movement of the wearer's knee during locomotion. The knee rail mechanism (27) can attach to calf beam (57) at attachment point (31). In some embodiments, a calf beam (57) can be disposed substantially parallel and anterior to the thigh beam (30). Accordingly, the calf beam (57) can have one end in fluid communication with the thigh beam (30) at the knee joint (34) and/or the knee rail mechanism (27). On an opposite end, calf beam (57) can be connected to or in fluid communication with the foot member (28). In this example, since the thigh beam (30) and the calf beam (57) are offset, a significant portion of the load (10) is being borne through the knee rail mechanism (27) as its transmitted to the floor.

In use, as shown in FIG. 13B, when a wearer of the load or protective garment (10) is standing straight, the knee rail (29) can be configured to resist bending of the knee joint (34). Alignment of the thigh beam (30) and the calf beam (57) can be such that the knee joint (34) is positioned on the knee rail (29) on the posterior side of the calf beam (57) to support the applied force from the load (10). This allows the load (10) to be borne through the thigh beam (30) and calf beam (57) and without the knee joint (34) buckling and transferring weight to the wearer. In the static position, point "B" on the knee rail mechanism (27) is where the thigh beam (30) engages the knee rail (29). In essence, the weight of the protective garment is distributed through the exoskeleton and supported, at least in part, by the knee rail mechanism (27) and the resistive element in turn holds the knee from bending. While standing straight, the wearer can be not moving or engaging in limited movement.

As shown in FIG. 13C, when the wearer's leg is lifted while in locomotion, alignment of the thigh beam (30) and the calf beam (57) can be shifted from point "B" to point "A" and the knee joint (34) slides on the knee rail (29) to a position on the anterior side of the calf beam (57). This allows the wearer to lift and bend one leg while the opposite leg (and its exoskeleton) supports, at least in part, the weight of load (10). In some embodiments, the knee rail (29) can be disposed at angle from 10 degrees to 80 degrees relative to a y-axis of the wearer. In a preferred embodiment, knee rail (29) can be disposed at angle of 45 degrees relative to a y-axis of the wearer. In some embodiments, the knee rail mechanism (27) can further include a stopper (33) configured to further restrict the knee joint (34) from bending.

Figure 14A:
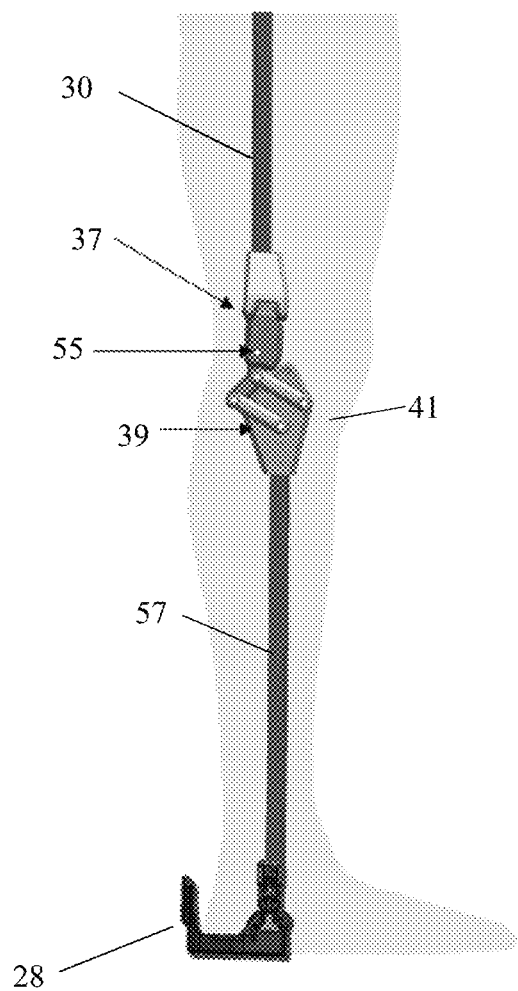
FIGS. 14A-14F illustrate configurations of yet another exemplary leg structure of the present invention.
Figure 14B:
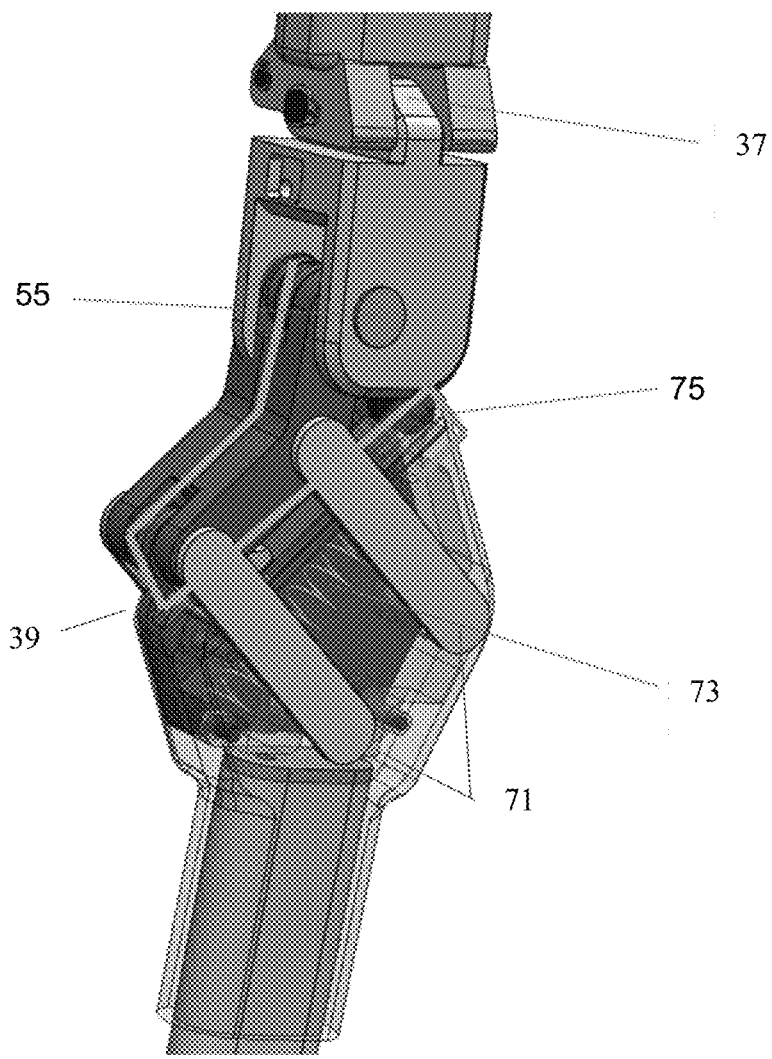

FIG. 14A shows an alternative leg structure for use with the exoskeleton. In this embodiment, each leg structure still includes a thigh beam (30). The thigh beam (30) can have one end attached to the pivot joint (26). In some embodiments, a lateral shifting hinge (37) can be in fluid communication with and/or attached to the thigh beam (30) on an end opposite of the pivot joint (26). The lateral shifting hinge (37) allows for lateral or horizontal movement of the leg structure. Hinge (37) can further be in fluid communication with or attached to knee lever mechanism (41). The knee lever mechanism (41) can further include a knee hinge (55) in fluid communication with and/or attached to the lateral shifting hinge (37). The knee lever mechanism (41) can further include lever (39). Lever (39) is a double or parallel lever, meaning that it includes at least two parallel rods (71). Lever (39) may shift or pivot to control the weight of protective garment (10). As shown in FIG. 14B, the knee lever mechanism (41) can further include a knee hinge resistive element (73). The resistive element can be a piston, spring, combinations thereof, or the like. Knee lever mechanism (41) can further include knee tension wire (75). It can be in fluid communication with and/or connected to thigh beam (30) on one end and the knee hinge resistive element (73) on an opposite end. The knee lever mechanism (41) can be in fluid communication with and/or attach to calf beam (57). In some embodiments, calf beam (57) can be disposed substantially parallel and anterior to the thigh beam (30). Accordingly, the calf beam (57) can have one end in fluid communication with the thigh beam (30) at the knee lever mechanism (41). On an opposite end, calf beam (57) can be connected to or in fluid communication with the foot member (28).

Figures 14C, 14D:
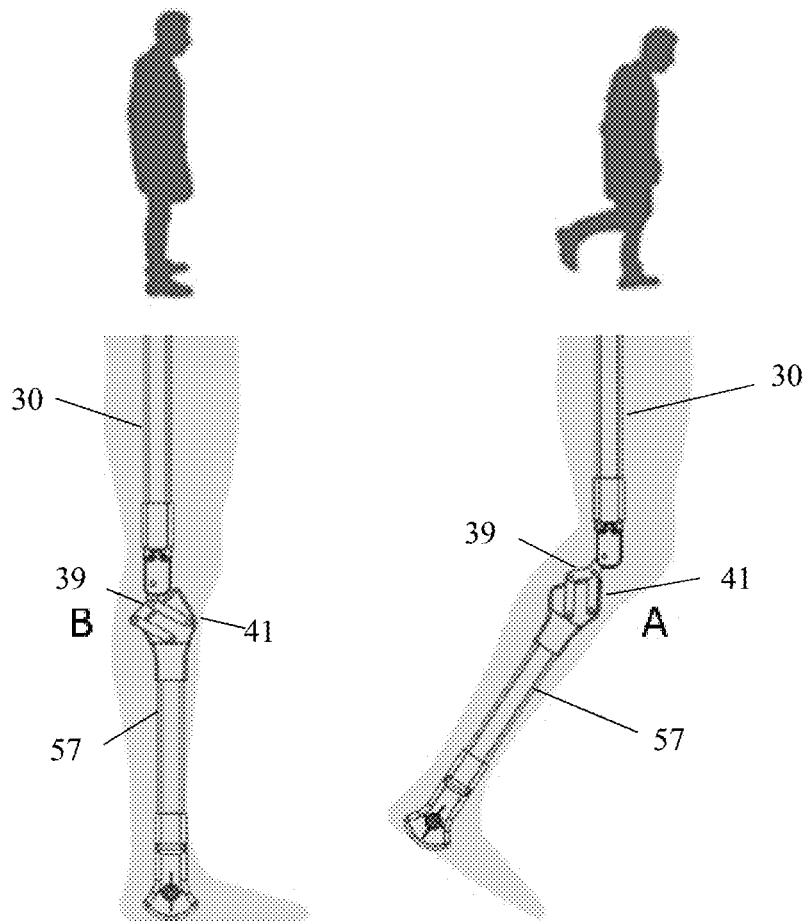

In use, as shown in FIG. 14C, when a wearer of the protective garment (10) is standing straight and not moving, the thigh beam (30) can be positioned at least partially behind the calf beam (57), the rods (71) of lever (39) can be positioned diagonally on the knee hinge (55), and the knee hinge resistive element (73) assists in creating a force to pull the lever (39) and shift the knee of a wearer to a bended position. Moreover, when the wearer leg is lifted in locomotion (FIG. 14D), the lever (39) is configured to shift to a threshold angle permitting bending of a knee of a wearer and transition the knee hinge (55) from a load-bearing position to a non-load bearing position. In essence, the weight of the protective garment is distributed through the exoskeleton and supported, at least in part, by the knee lever mechanism (41). When the wearer's leg is lifted in locomotion, the lateral shifting hinge can shift up to 50 degrees, from 180 degrees to 230 degrees, in a direction away from the wearer.

Figure 14E:
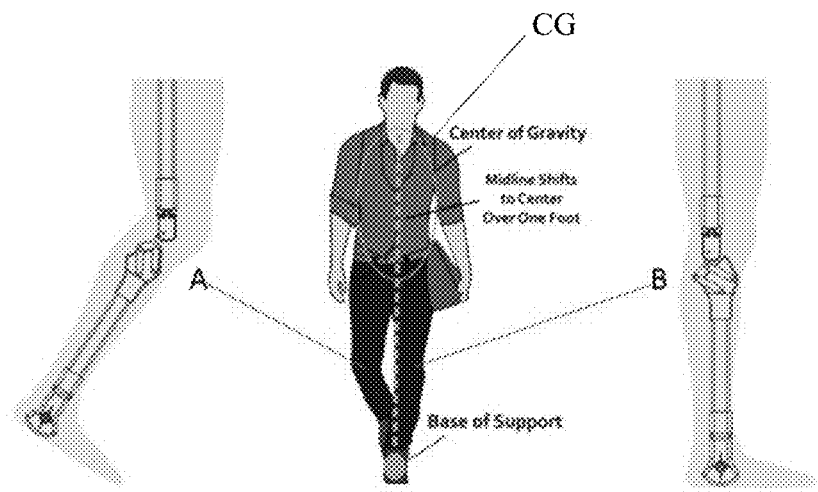
Figure 14F:
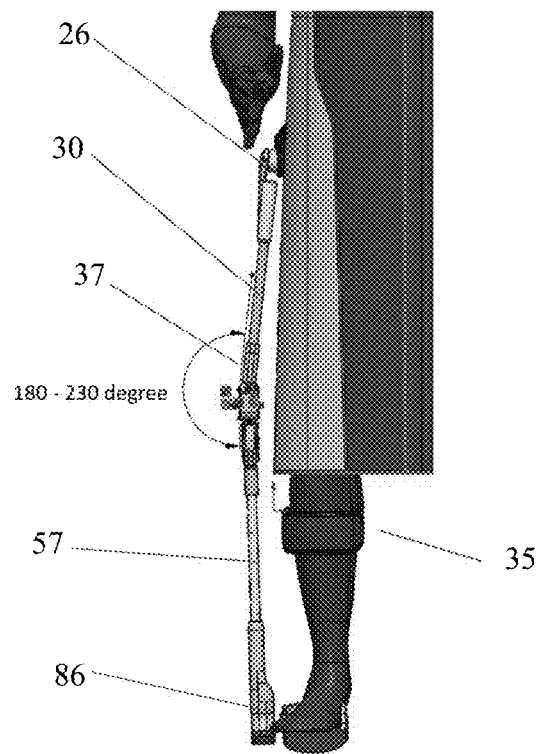

FIGS. 14E and 14F illustrate the wearer in locomotion and standing static in the anterior and lateral views. The wearer's knee has the natural tendency for lateral movement when the wearer is both moving and still. FIG. 14E illustrates a wearer's center of gravity (CG) and as the wearer walks, naturally one leg will shift toward the center of gravity (CG) to allow the use to remain balanced as weight shifts from one leg to the other. Lateral shifting hinge (37) compensates for that movement, whereas in the previous example, the knee joint 34 had the ability to just rotate over the knee rail 29, especially as it moves from point "B" to "A" and back again. In FIG. 14E, right leg is non-load bearing leg due to center of gravity shifts during locomotion. Exoskeleton knee is in position A. Left leg is load-bearing leg due to center of gravity shifts during locomotion. Exoskeleton knee is in position B.

FIG. 14F illustrates an anterior section view of the wearer standing static. Here, the lateral shifting hinge (37) is providing some "flex" as it allows for lateral movement, even as the wearer stands. Most wearers will shift their weight from foot to foot as they stand, move their feet from outside their shoulder width, to parallel with their shoulder width and even begin to get their feet close enough to touch heels. The lateral shifting hinge (37) permits that movement, all while still bearing the load (10). This all bears in mind that the wearer is "locked" into the exoskeleton at a number of critical points, heel, shin, hip, and shoulders, weight needs to be transferred from the shoulders to the floor, but the wearer still needs the largest, unencumbered, range and freedom of motion.

In any instance of a wearer using the exoskeleton, fine to gross movements are critical. Two examples are neurosurgeon and an emergency responder. In the neurosurgeon example, the wearer can perform neurovascular procedures in which tiny devices are being tracked up from a patient's femoral artery in the groin, through the heart and into the fine vasculature of the brain. Fluoroscopy (continuous x-ray) is needed to track the device as it travels through the patient and very fine movements are needed to complete the procedure, all while wearing a protective garment 10. In contrast, an emergency responder responding to, for example, an incident at a nuclear power plant, is required to make gross movements to help move equipment or components and is likely carrying other tools and equipment. Fine movements may also be needed from the same responder to work with computers, electrical systems, and/or provide medical assistance to exposed persons. The exoskeleton system in these examples need to provide for all contingencies of static and moving conditions, all while bearing as much of the load (10) as possible.

Figure 15A:
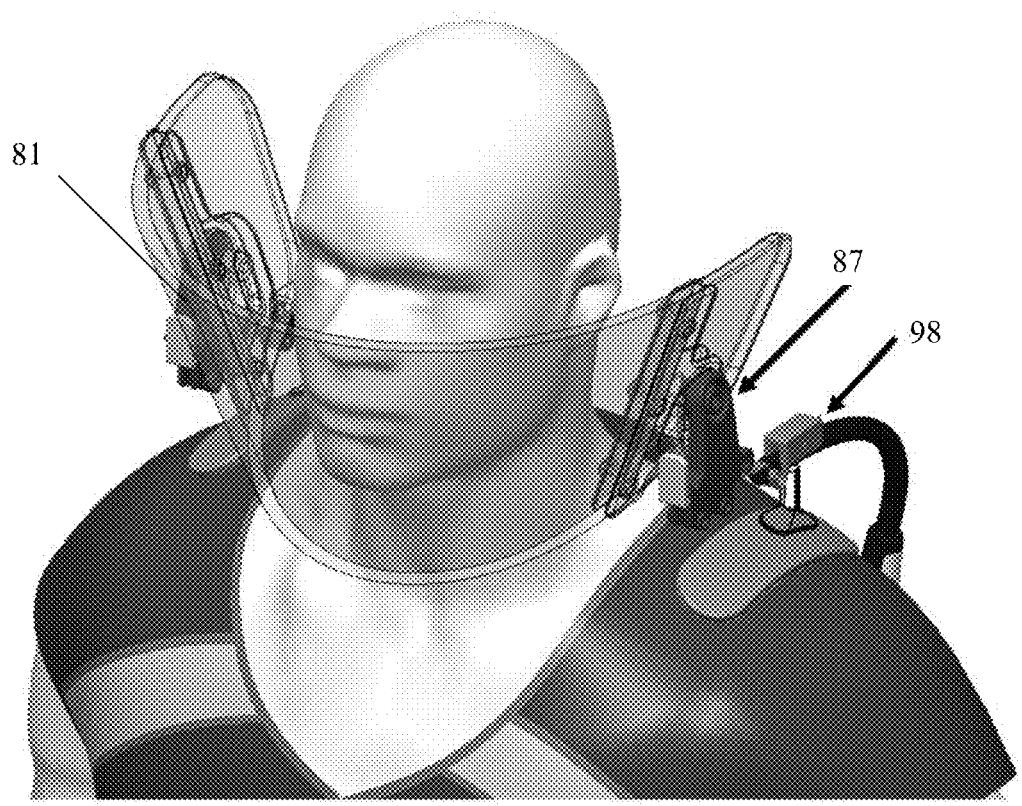
FIGS. 15A-15D illustrate configurations of another exemplary face shield of the present invention.
Figure 15B:
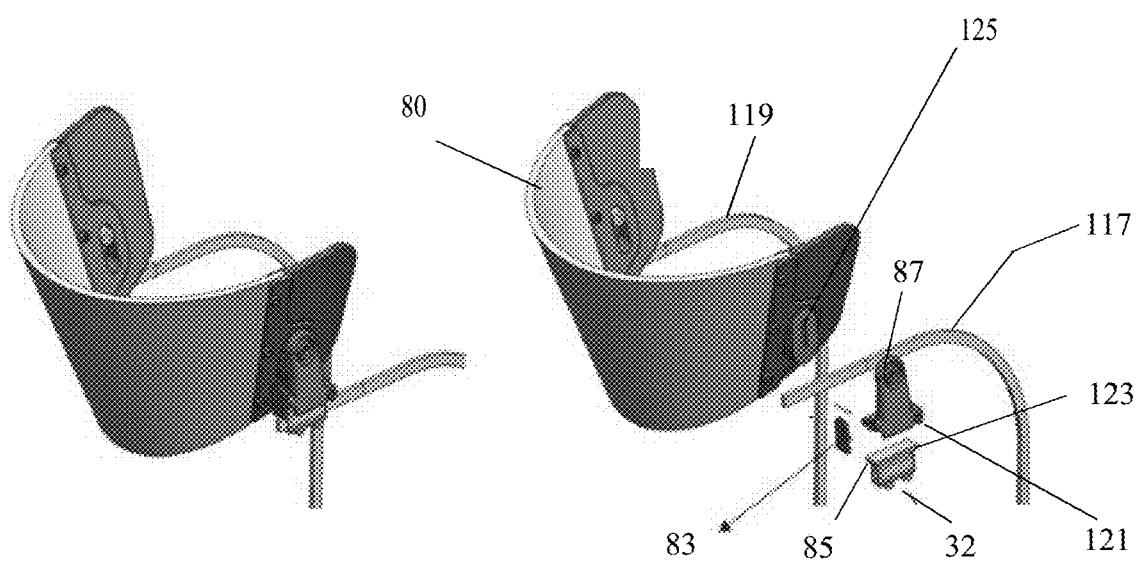

The exoskeleton system can also incorporate support for protective gear for the face and head of the wearer. In one embodiment, as shown in FIGS. 15A-B, the face shield (80) may be attached to the caudal member (64) by at least one shoulder attaching rail (117, 119). In other embodiments, the face shield (80) is attached to the caudal member (64) by multiple static balancing rods. The face shield (80) can be mounted to the right shoulder attaching element (not shown). In use, the face shield (80) can be mounted such that the weight of the face shield (80) is distributed from the neck and back and primarily to the floor through the exoskeleton (20) and supported, at least partially, proximate the knee of the user, while permitting freedom of movement of a face and a head of the wearer.

In one example, the face shield (80) can be mounted to left shoulder attaching rail (117) by engaging left adjusting hinge (87). In some embodiments, face shield (80) can include left adjusting hinge receiving member (125). Left adjusting hinge (87) can attach to left adjusting hinge receiving member (125) and be fastened to it by any suitable means (e.g. screw, pin, rivet). As shown in FIG. 15B, left adjusting hinge (87) can include a left clip (83) and left adjusting hinge spring-loaded member (121). Left adjusting hinge (87) can mate with left shoulder attaching element (32), which includes a left clip mating member (85) and a left adjusting hinge spring mating member (123). To engage, left adjusting hinge spring-loaded member (121) mates with left adjusting hinge spring mating member (123) and left clip (83) mates with left clip mating member (85). Left shoulder attaching element (32) can be mounted on left shoulder attaching rail (117) by any suitable means (e.g. aperture disposed therein, track, friction-fit).

Figure 15C:
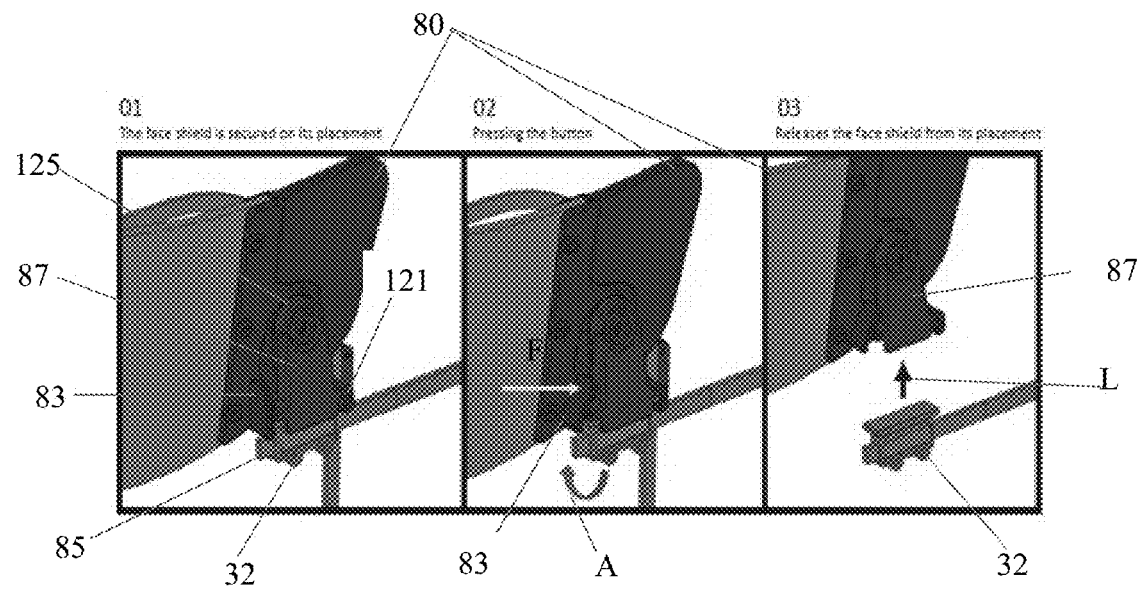

As shown in FIG. 15C, left clip (83) can be further configured to create a positive lock with left clip mating member (85), and in some embodiments, be configured to be released from left clip mating member (85) when pressed. Similarly, the face shield (80) can be mounted to right shoulder attaching rail (119) by engaging right adjusting hinge (81). In some embodiments, face shield (80) can include a right adjusting hinge receiving member. Right adjusting hinge (81) can attach to the right adjusting hinge receiving member and be fastened to it by any suitable means (e.g. screw, pin, rivet). Right adjusting hinge (81) can include a right clip and a right adjusting hinge spring-loaded member. Right adjusting hinge (81) can mate with right shoulder attaching element (not shown), which can include a right clip mating member and a right adjusting hinge spring mating member. To engage, right adjusting hinge spring-loaded member mates with right adjusting hinge spring mating member and right clip mates with right clip mating member. Right shoulder attaching element (not shown) can be mounted on right shoulder attaching rail (119) by any suitable means (e.g. aperture disposed therein, track, friction-fit). The right clip can be further configured to create a positive lock with right clip mating member, and in some embodiments, be configured to be released from right clip mating member when pressed.

FIG. 15C further illustrates the detachment sequence to detach the face shield (80) from the left shoulder attaching rail (117). Note that a similar or mirror image sequence can be performed for the right side of the wearer. The left diagram in FIG. 15C illustrates the left adjusting hinge (87) secured to both the left adjusting hinge receiving member (125) and the left shoulder attaching element (32). The left adjusting hinge (87) can be both pivotally and slidingly engaged in the left adjusting hinge receiving member (125). In one example, the left adjusting hinge (87) and the left adjusting hinge receiving member (125) are fixedly attached, while in other examples they can be removably attached. When engaged, the left clip (83) is locked onto the left clip mating member (85) while the left adjusting hinge spring mating member (123) engages the left adjusting hinge receiving member (125). In this example, the left adjusting hinge receiving member (125) is a fixed lip and the left adjusting hinge spring mating member (123) is a "hook" shape to catch the lip. The left clip (83) catches a similar lip on the left clip mating member (85).

The middle diagram in FIG. 15C illustrates the first part of the detachment sequence. Force (F) is applied to the left clip (83), and in this example, it pivots to disengage the left clip mating member (85) or it can be said that the left clip (83) moves to an "unlocked" position. Here, the left clip (83) can be spring loaded to return to its "locked" position once the force (F) is removed. Once the left clip (83) disengages the left clip mating member (85), the left adjusting hinge (87) can be tilted/rotated/pivoted/angled (A) upwards to allow the left adjusting hinge receiving member (125) to disengage the left adjusting hinge spring mating member (123). Once the left clip (83) and the left adjusting hinge receiving member (125) are disengaged from their respective mates on the left shoulder attaching element (32) the face shield (80) and the left adjusting hinge (87) can be lifted (L) away, as shown in the right diagram in FIG. 15C. In an alternate example, the left clip (83) can be fixed and the left adjusting hinge spring-loaded member (121) can be spring-loaded and moves horizontally. Here, the left adjusting hinge (87) can be pulled forward to move the left adjusting hinge spring-loaded member (121) far enough to release the left clip (83), the left adjusting hinge (87) rotated and lifted, as in the previous examples.

Figure 15D:
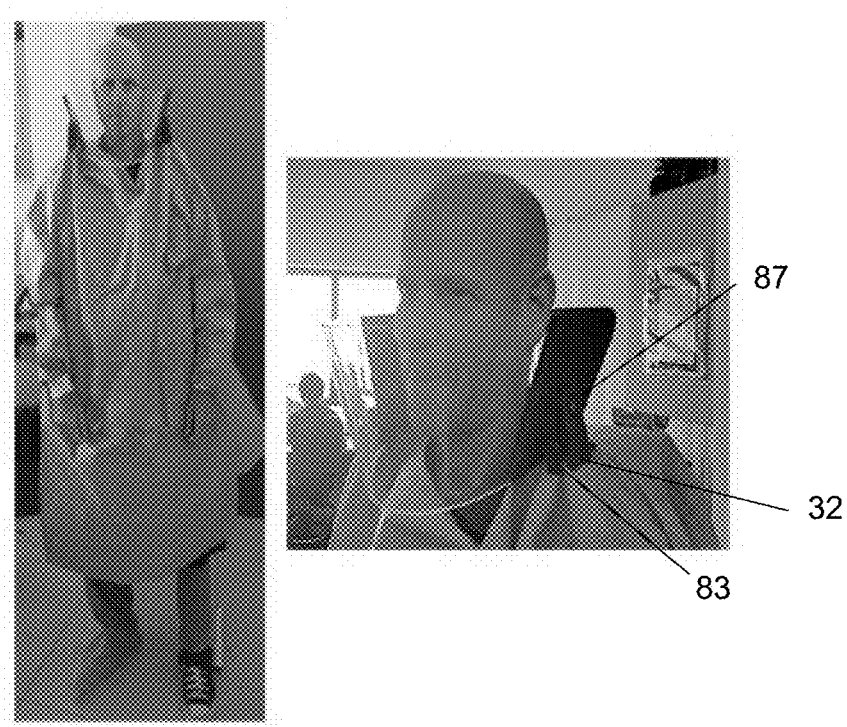

In some embodiments, as shown in FIG. 15D, the right shoulder attaching element (not shown) is configured to attach to the right adjusting hinge (81) and the left shoulder attaching element (32) is configured to attach to the left adjusting hinge (87) with a surgical gown disposed therebetween. Note that in one example of use, the exoskeleton and protective garment (10) are disposed under the wearer's sterile garment. However, the face shield (80) is typically donned last (after gowning) and worn outside the gown. In some embodiments, the right adjusting hinge (81) is configured to create a positive lock with the right shoulder attaching element (not shown) and the left adjusting hinge (87) is configured to create a positive lock with the left shoulder attaching element (32) without tearing the surgical gown. Moreover, the face shield (80) may be taken on and off several times without tearing the sterile gown. This is an important feature, as any tear in the gown can lead to further tears as an operation progresses but further allows the wearer additional flexibility if the face shield (80) becomes difficult to see through.

In still some embodiments, the shield (80) can include a left adjusting rail (98) and a right adjusting rail. The rails control the how the shield (80) pivots about on the right adjusting hinge (81) and the left adjusting hinge (87). Each rail can be configured to position the shield (80) anterior the face of the wearer, posterior the face of the wearer, or some combination thereof.

Figure 16A:
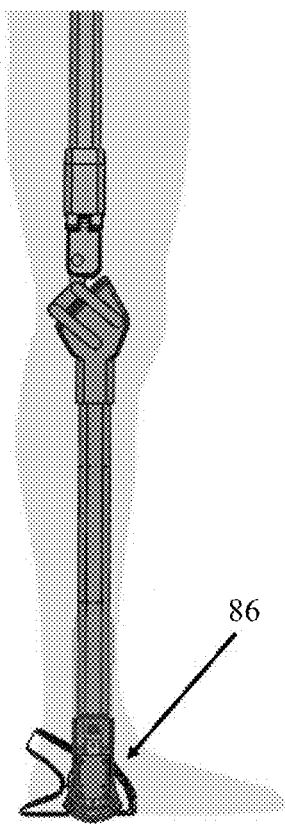
FIGS. 16A-16F illustrate configurations of another exemplary foot joint mechanism of the present invention.
Figure 16B:
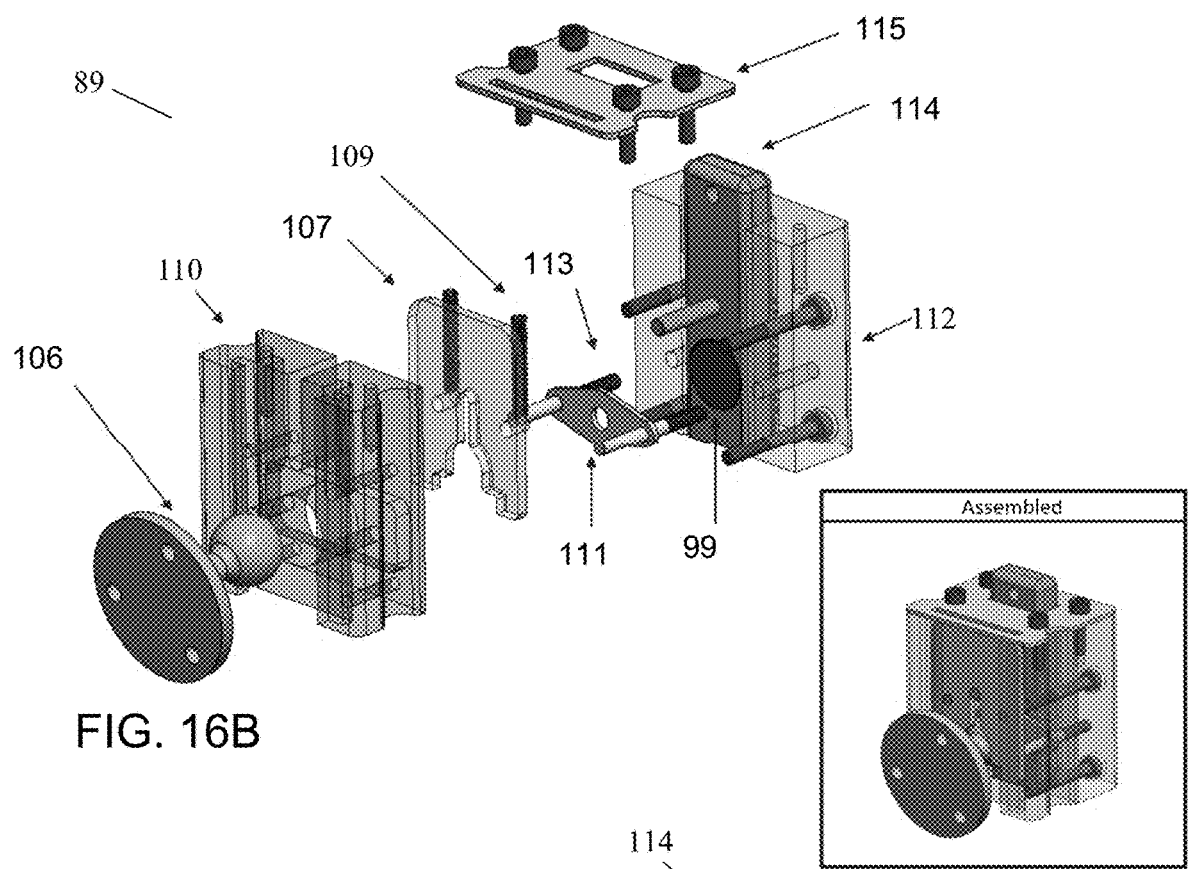
Figure 16C:
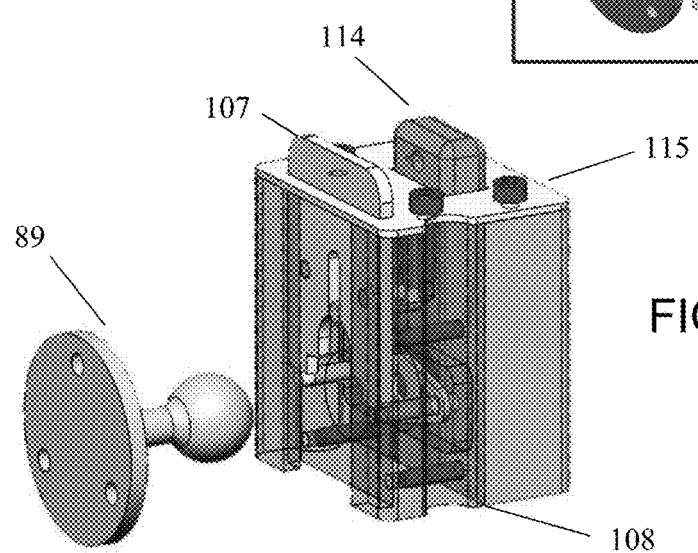
Figure 16D:
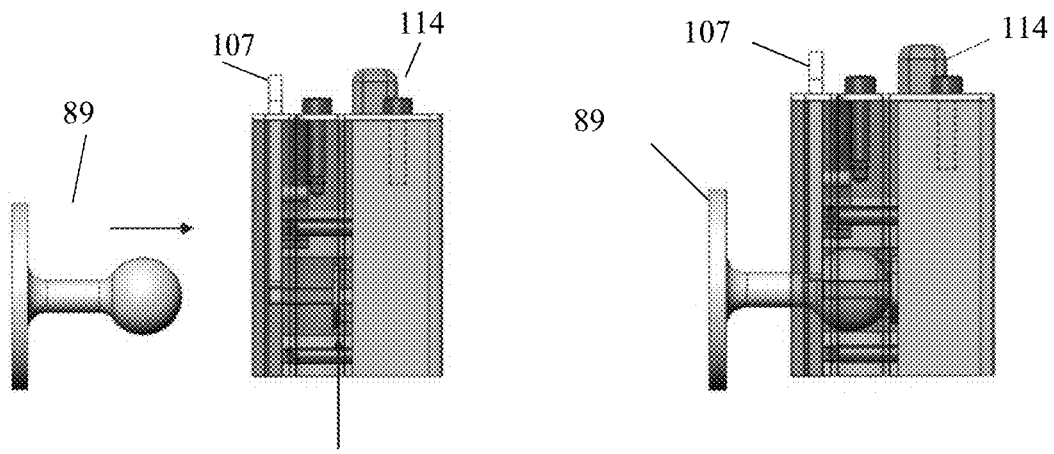

In one embodiment, as shown in FIG. 16A, the shoe holster (28) can include and be attached to the calf beam (57) by a magnetic ball joint system (89). FIG. 16B shows the system (89) disassembled and including a ball (106) and a quick release mechanism (108). In some embodiments, quick release mechanism (108) can include a magnet (99). The ball (106) is configured to be drawn into the quick release mechanism (108) and engage the magnet (99). In an exemplary embodiment, the quick release cable (53) would extend high enough to be within grasp of the wearer and be configured such that the wear could pull the cable to disengage the ball (106) from the quick release mechanism (108). The quick release mechanism (108) can further include a ball joint housing (110) configured to receive and matingly engage the ball joint. Mechanism (108) also includes a magnet housing (112) including magnet (99) and magnet puller (114). There is also locking slider (107) as part of mechanism (108) and it includes a locking slider resistive element (109), a lock pins plate (111) including a lock pins plate resisting element (113), and an upper plate (115). As shown in FIGS. 16C-16D, as the ball (106) is attracted to magnet (99), it is configured to enter and matingly engage the ball joint housing (110), push the lock pins plate (111) towards the magnet housing (112), and release the locking slider (107) from a locked position. The use of the magnet (99) and ball (106) can be switched, wherein the ball (106) is magnetic and the magnet (99) is a magnetic material. The use of magnetic attraction allows the system (89) to be generally self-aligning for engagement and eases the wearer's "suiting up" time.

Figure 16E:
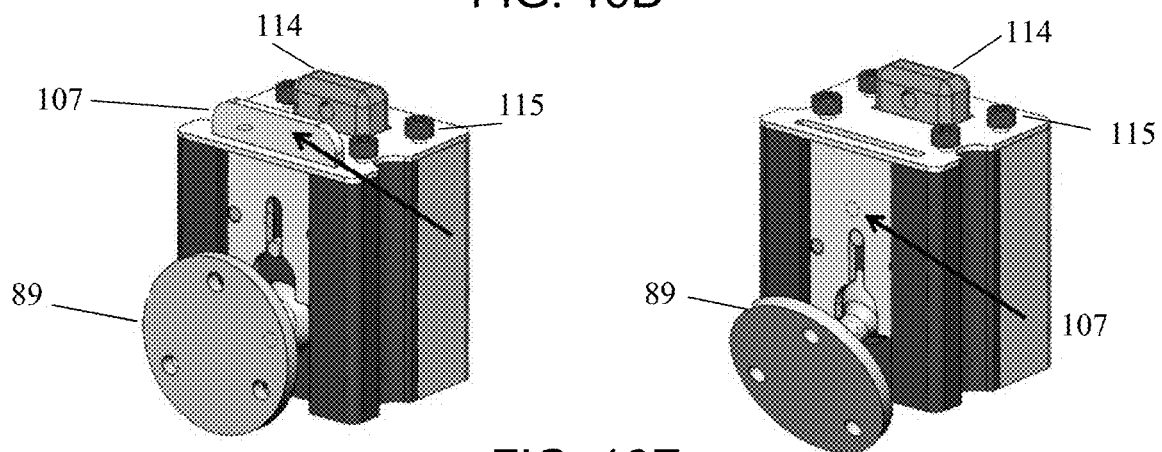
Figure 16F:
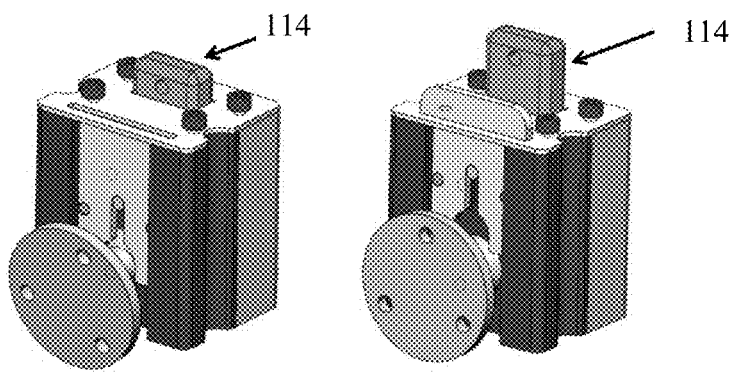

As shown in FIG. 16E, once the ball (106) and ball joint housing (110) are matingly engaged, the locking slider (107) is configured to move in a downward direction to lock the ball (106) into the quick release mechanism (108). The system can also include quick release cable (53), further configured to actuate the release of the ball (106) from the quick release mechanism (108). As shown in FIG. 16F, to disengage, the magnet puller can be configured to pull the locking slider (107) and the magnet (99) in an upward direction to a raised position, breaking the magnetic attraction and releasing the ball (106) from the quick release mechanism (108). When the ball (106) is not engaged with the quick release mechanism (108), the lock pins plates (111) are configured to lock the locking slider (107) in the raised position.

The following clauses list non-limiting examples of the disclosure:

1. A weight-distribution exoskeleton system, comprising: a load (10); and an exoskeleton (20) configured to engage the load (10) and having a plurality of leg structures (24), each leg structure comprising: a pelvis joint (26); and a foot member (28) configured to attach to a foot of a wearer of the load (10), wherein the exoskeleton provides a hanging force to counteract at least some weight of the load (10) when an applied force from the load (10) is encountered, the applied force from the load (10) being at least partially transmitted to a floor through the foot member (28).
2. A weight-distribution exoskeleton system, comprising: a load (10) having a surface; and an exoskeleton (20) configured to engage the surface of the load (10) and having a plurality of leg structures (24), each leg structure comprising: a pelvis joint (26); and a foot member (28) configured to attach to a foot of a wearer of the load (10), wherein the exoskeleton provides a hanging force to counteract at least some weight of the load (10) when an applied force from the load (10) is encountered, the applied force from the load (10) being at least partially transmitted to a floor through the foot member (28).
3. The weight-distribution exoskeleton system of clause 2, wherein the surface includes at least one of an inner surface and an outer surface of the load.
4. The weight-distribution exoskeleton system of clause 1, wherein the load comprises a personal protective equipment, wherein the personal protective equipment includes one or more of the following: a protective garment, a gear, a helmet, and a google.
5. The weight-distribution exoskeleton system of clause 1, wherein the load includes: a plurality of upper body receiving elements (12) attached to an upper surface of the load (10).
6. The weight-distribution exoskeleton system of clause 1, wherein the load includes: a pelvic attachment belt (14) disposed on an inner, pelvic surface of the load (10).
7. The weight-distribution exoskeleton system of clause 6, wherein the load includes: a plurality of pelvis rails (16) mounted on an outer, pelvic surface of the load (10) or mounted on the pelvic attachment belt, and comprising a lockable pelvis joint mechanism (18) slidably received by the pelvis rails (16).
8. The weight-distribution exoskeleton system of clause 6, wherein the pelvic attachment belt (14) can be configured to stabilize the exoskeleton system on the wearer of the load.
9. The weight-distribution exoskeleton system of clause 7, wherein the lockable pelvis joint mechanism (18) is configured to permit sizing adjustments of the wearer.
10. The weight-distribution exoskeleton system of clause 4, wherein the protective garment (10) can be an ionizing radiation protective garment, an x-ray protective garment, a gamma protective garment, or a ballistics protective garment.
11. The weight-distribution exoskeleton system of clause 5, wherein each of the upper body receiving elements (12) comprises a floating arc (11) attached to an inner, shoulder area of the protective garment (10), a bridge component (13) attached to an outer, shoulder area of the protective garment (10) above the floating arc (11), and receiving component (15) formed with an orifice to receive an upper body attaching element (22, 32) and attached to the bridge component (13) by a ball joint (17).
12. The weight-distribution exoskeleton system of clause 11, wherein the floating arc (11) is rigid or semi-rigid.

13. The weight-distribution exoskeleton system of clause 4, wherein the protective garments comprise a plurality of upper body attaching elements (22, 32), a right shoulder attaching element (22) and a left shoulder attaching element (32).
14. The weight-distribution exoskeleton system of clause 1, wherein a majority of the load counteracted by the exoskeleton is on an anterior side of the wearer.
15. The weight-distribution exoskeleton system of clause 5, wherein at least one of the plurality of upper body receiving elements (12) can comprise a ladder adjustment mechanism (19, 23) configured to removably engage at least one of a clips element (21, 25).
16. The weight-distribution exoskeleton system of clause 7, wherein at least one of the plurality of pelvis rails (16) can comprise a ladder adjustment mechanism (19, 23) configured to removably engage at least one of a clips element (21, 25).
17. The weight-distribution exoskeleton system of clause 1, each leg structure further comprising: a thigh beam (30) having one end attached to the pelvis joint (26); a knee joint (34) attached to the thigh beam (30) on an end opposite of the pelvis joint (26); a resistive element (36) disposed posterior to the thigh beam (30) and having a bottom end (38); a threshold rail (40) disposed below and having one end attached to the knee joint (34); a pushing rail (44) disposed below the threshold rail (40); a collapsing hinge (46) having a front attachment point (48), a middle attachment point (50), and a back attachment point (52), the front attachment point (48) connected to the pushing rail (44) and the back attachment point (52) connected to the resistive element (36); a collapse resistance spring (54) mounted on the collapsing hinge (46) near the back attachment point (52); a calf rail (56) disposed substantially parallel and posterior to the pushing rail (44) and having one end connected to the thigh beam (30) at the knee joint (34) and an opposite end connected to the shoe holster (28); and a resistive element slider (58) disposed on the calf rail (56) and connected to the collapsing hinge (46) at the middle attachment point (50) and further attached to the bottom end of the resistive element (36), wherein the threshold rail (40) is curved to extend downward between the calf rail (56) and the pushing rail (44).
18. The weight-distribution exoskeleton system of clause 17, wherein when a wearer of the protective garment (10) is standing, the resistive element (36) is configured to prevent the knee joint (34) from bending.
19. The weight-distribution exoskeleton system of clause 18, wherein the shoe holster (28) comprises a walking sensor (60) configured to slide from inside the shoe holster (28) down to outside the shoe holster (28) when a leg of the wearer of the protective garment (10) is lifted.
20. The weight-distribution exoskeleton system of clause 19, wherein once the walking sensor (60) slides down to outside of the shoe holster (28), the pushing rail (44) is configured to be driven up towards the collapsing hinge (46), positioning the collapsing hinge (46) against the threshold rail (40) at a threshold point (62).
21. The weight-distribution exoskeleton system of clause 20, wherein when the wearer's leg bends while walking, the collapsing hinge (46) is configured to move past the threshold point (62), collapse, and permit bending of a knee of a wearer.
22. The weight-distribution exoskeleton system of clause 21, wherein when the wearer's leg bends while sitting, the walking sensor (60) is configured to lock such that the pushing rail (44) and the collapsing hinge (46) do not engage and the resistive element (36) is configured to contract and provide a supportive force to counteract at least some weight of the protective garment (10) when the applied force from the protective garment (10) is encountered, the applied force from the protective garment (10) being at least partially transmitted to the floor through the shoe holster (28).
23. The weight-distribution exoskeleton system of clause 22, further including a caudal member (64) connecting the right shoulder attaching element (22) and the left shoulder attaching element (32) to the pelvis joints (26).
24. The weight-distribution exoskeleton system of clause 23, wherein the caudal member (64) includes a left beam (66) attaching the left shoulder attaching element (32) to the pelvis joint (26) of one of the leg structures and a right beam (68) attaching the right shoulder attaching element (22) to the pelvis joint (26) of another of the leg structures, and a central beam (70) extending between the left beam (66) and the right beam (68).
25. The weight-distribution exoskeleton system of clause 24, wherein a static face shield (72) is attached to the caudal member (64) by at least one first balancing rod (74), at least shoulder attaching element, or a combination thereof.
26. The weight-distribution exoskeleton system of clause 24, wherein a visor face shield (76) is attached to the caudal member (64) by a second balancing rod (78) comprising at least one of a tension spring, a compression spring, or motion sensitive control, the second balancing rod (78) configured to distribute the weight of the visor face shield (76) through the exoskeleton (20) and to the floor while permitting freedom of movement of a face and a head of the wearer.
27. The weight-distribution exoskeleton system of clause 24, wherein a semi-rigid face shield (80) is pivotally mounted to the right shoulder attaching element (22) by a right rotational joint (82) and the left shoulder attaching element (32) by a left rotational joint (84) such that the weight of the semi-rigid face shield (80) is distributed through the exoskeleton (20) and to the floor while permitting freedom of movement of a face and a head of the wearer.
28. The weight-distribution exoskeleton system of clause 24, wherein the shoe holster (28) is attached to the calf rail (56) by a first modified ball joint (86).
29. The weight-distribution exoskeleton system of clause 24, wherein the pelvis joint (26) is attached to the lockable pelvis joint mechanism (18) by a second modified ball joint (88).
30. The weight-distribution exoskeleton of clause 28, wherein the first modified ball joint (86) comprises a quick release mechanism.
31. The weight-distribution exoskeleton of clause 30, wherein the second modified ball joint (88) comprises a quick release mechanism.
32. A weight-distribution exoskeleton, comprising: a load attachment mechanism (22, 32); and a plurality of leg structures (24), each leg structure comprising: a pelvis joint (26) configured to attach the leg structure (24) to an outer surface of a load (10) near a pelvis area of a wearer of the protective garment (10); and a foot member (28) configured to attach to a foot of a wearer of the protective garment (10), wherein the load attachment mechanism (22, 32) provides a hanging force to counteract at least some weight of the protective garment (10) when an applied force from the protective garment (10) is encountered, the applied force from the protective garment (10) being at least partially transmitted to a floor through the foot member (28).

33. A weight-distribution exoskeleton system, comprising: a load; and an exoskeleton configured to engage the load and having a plurality of leg structures, each leg structure comprising: a pivot joint proximate the pelvis of a wearer of the load; a knee mechanism proximate the knee of the wearer; and a foot member configured to attach to a foot or shoe of the wearer, wherein the exoskeleton provides a hanging force to counteract at least some weight of the load when an applied force from the load is encountered, the applied force from the load being at least partially supported by the knee rail mechanism and transferred to the floor.

34. The weight-distribution exoskeleton system of clause 28, each leg structure further comprising: a thigh beam having one end attached to the pivot joint; a knee joint attached to the thigh beam on an end opposite of the pivot joint; the knee mechanism including a knee rail and an attachment point; a shin mechanism proximate the shin of the wearer, wherein the knee joint is disposed on and slidingly engages the knee rail on an end opposite the attachment point; and a calf beam connected to the knee rail mechanism at the attachment point at one end and having an opposite end in fluid communication with the foot member.

35. The weight-distribution exoskeleton system of clause 34, wherein when a wearer of the protective garment is standing straight and not moving, alignment of the thigh beam and the calf beam such that the knee joint is positioned on the knee rail on the posterior side of the calf beam to support the applied force from the load.

36. The weight-distribution exoskeleton system of clause 34, wherein when the wearer's leg is lifted while in locomotion, alignment of the thigh beam and the calf beam is shifted to a and the knee joint slides on the knee rail to a position on the anterior side of the thigh beam.

37. The weight-distribution exoskeleton system of clause 34, wherein the knee rail is disposed at angle from 10 degrees to 80 degrees relative to a y-axis of the wearer.

38. The weight-distribution exoskeleton system of clause 34, wherein the knee rail mechanism further comprises a stopper configured to restrict the knee joint from bending.

39. A weight-distribution exoskeleton system, comprising: a load; and an exoskeleton configured to engage the load and having a plurality of leg structures, each leg structure comprising: a pivot joint proximate the pelvis of a wearer of the load; a knee lever mechanism proximate the knee of the wearer; and a foot member configured to attach to a foot or shoe of the wearer, wherein the exoskeleton provides a hanging force to counteract at least some weight of the load when an applied force from the load is encountered, the applied force from the load being at least partially supported by the knee lever mechanism.

40. The weight-distribution exoskeleton system of clause 39, each leg structure further comprising: a thigh beam having one end attached to the pivot joint; a lateral shifting hinge attached to the thigh beam on an end opposite of the pivot joint; a knee hinge attached to the lateral shifting hinge and including a lever with at least two parallel rods, a knee hinge resistive element, and a knee tension wire connected to the thigh beam on one end and the knee hinge spring on an opposite end; a shin mechanism proximate the shin of the wearer; and a calf beam in fluid communication with the knee hinge at one end and in fluid communication with the foot member at an opposite end.

41. The weight-distribution exoskeleton system of clause 40, wherein when a wearer of the protective garment is standing straight and not moving, the thigh beam is positioned at least partially behind the calf beam, the rods of lever are positioned diagonally on the knee hinge, and the knee hinge resistive element assists in creating a force to pull the lever and shift the knee of a wearer to a bended position.

42. The weight-distribution exoskeleton system of clause 40, wherein when the wearer leg is lifted in locomotion, the lever is configured to shift to a threshold angle permitting bending of a knee of a wearer and transition the knee hinge from a load-bearing position to a non-load bearing position.

43. The weight-distribution exoskeleton of clause 40, wherein when the wearer leg is lifted in locomotion, the lateral shifting hinge shifts up to 50 degrees, from 180 degrees to 230 degrees, in a direction away from the wearer.

44. The weight-distribution exoskeleton system of clause 40, wherein the shin mechanism includes a shin cuff member at least partially surrounding a shin of the wearer and includes a shin strap configured to hold the shin cuff member onto the shin of the wearer, a vertical teeth component, a horizontal teeth component, a release hook, and a quick release cable connected to the vertical teeth component, wherein the horizontal teeth component and the vertical teeth component are configured to engage, and the release hook is configured to hold the horizontal teeth component and the vertical teeth component in engagement, securing the shin strap and shin cuff member on the shin of the wearer, and wherein the quick release cable is configured to pull the vertical teeth component, thereby causing the horizontal teeth component to move and disengage the shin strap releasing the shin cuff member from the shin of the wearer.

45. The weight-distribution exoskeleton system of clause 44, wherein the protective garment can be an ionizing radiation protective garment, an x-ray protective garment, a gamma protective garment, or a ballistics protective garment.

46. The weight-distribution exoskeleton system of clause 33, wherein a majority of the load counteracted by the exoskeleton is on an anterior side of the wearer.

47. The weight-distribution exoskeleton system of clause 33, further including a caudal member connecting the right shoulder attaching element and the left shoulder attaching element to the pivot joints.

48. The weight-distribution exoskeleton system of clause 47, wherein the caudal member includes a left beam attaching the left shoulder attaching element to the pivot joint of one of the leg structures and a right beam attaching the right shoulder attaching element (not shown) to the pivot joint of another of the leg structures, and a central beam extending between the left beam and the right beam.

49. The weight-distribution exoskeleton system of clause 48, further comprising a face shield pivotally mounted to the right shoulder attaching element by a right adjusting hinge and pivotally mounted to a left shoulder attaching element by a left right adjusting hinge, each adjusting hinge configured to adjust a tilt angle of the shield.

50. The weight-distribution exoskeleton system of clause 49, wherein the right shoulder attaching element is configured to attach to the right adjusting hinge and the left shoulder attaching element is configured to attach to the left adjusting hinge with a surgical gown disposed therebetween.

51. The weight-distribution exoskeleton system of clause 50, wherein the right adjusting hinge is configured to create a positive lock with the right shoulder attaching element (not shown) and the left adjusting hinge is configured to create a positive lock with the left shoulder attaching element without tearing the surgical gown.

52. The weight-distribution exoskeleton system of clause 51, wherein the right adjusting hinge is configured to create a positive lock with the right shoulder attaching element (not shown) and the left adjusting hinge is configured to create a positive lock with the left shoulder attaching element without tearing the surgical gown.

53. The weight-distribution exoskeleton system of clause 49, further comprising a left adjusting rail and a right adjusting rail, each rail configured to position the shield anterior the face of the wearer or posterior the face of the wearer.

54. The weight-distribution exoskeleton system of clause 33, wherein the shoe holster is attached to the calf beam by a magnetic ball joint system including a magnetic ball joint and a quick release mechanism including a magnet, wherein the magnetic ball joint is configured to be drawn into enter the quick release mechanism and engage the magnet.

55. The weight-distribution exoskeleton of clause 54, wherein the quick release mechanism includes a ball joint housing, a magnet housing including the magnet and a magnet puller, and locking slider including a locking slider resistive element, a lock pins plate including a lock pins plate resisting element, and an upper plate, wherein the magnetic ball joint is configured to enter the ball joint housing, push the lock pins plate towards the magnet housing, release the locking slider from a locked position, and engage the magnet.

56. The weight-distribution exoskeleton of clause 55, wherein the locking slider is configured to move in a downward direction to lock the ball joint into the quick release mechanism.

57. The weight-distribution exoskeleton of clause 56, wherein in the magnet puller is configured to pull the locking slider and the magnet in an upward direction to a raised position and to release the ball joint from the quick release mechanism.

58. The weight-distribution exoskeleton of clause 57, wherein when the ball joint is not engaged with the quick release mechanism, the lock pins plates is configured to lock the locking slider in the raised position.

59. A knee rail system for supporting a load on a wearer, comprising: a knee rail; an attachment point connected to a calf beam; and a knee joint attached to a thigh beam, wherein the knee joint is disposed on and slidingly engages the knee rail on an end opposite the attachment point.

60. The knee rail system of clause 59, wherein the knee rail system is positioned proximate to a knee of the wearer.

61. The knee rail system of clause 59, wherein when the wearer is standing straight and not moving, the thigh beam and the calf beam are aligned, and that the knee joint is positioned on the knee rail on a posterior side of the calf beam to support an applied force from the load.

62. The knee rail system of clause 59, wherein when the wearer's leg is lifted while in locomotion, the knee joint slides on the knee rail to a position on an anterior side of the thigh beam.

63. The knee rail system of clause 59, wherein the knee rail is disposed at angle from 10 degrees to 80 degrees relative to a y-axis of the wearer.

64. The knee rail system of clause 59, further comprising a stopper configured to restrict the knee joint from bending.

65. A knee lever system for supporting a load on a wearer, comprising: a lateral shifting hinge attached to a thigh beam; a knee hinge attached to the lateral shifting hinge and including a lever with at least two parallel rods, a knee hinge resistive element, and a knee tension wire connected to the thigh beam on one end and the knee hinge spring on an opposite end, wherein the knee hinge is in fluid communication with a calf beam.

66. The knee lever system of clause 65, wherein the knee lever system is positioned proximate to a knee of the wearer.

67. The knee lever system of clause 65, wherein when the wearer is standing straight and not moving, the thigh beam is positioned at least partially behind the calf beam, the rods of lever are positioned diagonally on the knee hinge, and the knee hinge resistive element assists in creating a force to pull the lever and shift a knee of the wearer to a bended position.

68. The knee lever system of clause 65, wherein when the wearer's leg is lifted in locomotion, the lever is configured to shift to a threshold angle permitting bending of a knee of the wearer and transition the knee hinge from a load-bearing position to a non-load bearing position.

69. The knee lever system of clause 65, wherein when the wearer leg is lifted in locomotion, the lateral shifting hinge shifts up to 50 degrees, from 180 degrees to 230 degrees, in a direction away from the wearer.

The descriptions contained herein are examples of embodiments of the invention and are not intended in any way to limit the scope of the invention. As described herein, the invention contemplates many variations and modifications of the exoskeletal systems, including varied positioning of the load and exoskeleton utilizing any of numerous materials for each element or member, incorporation of additional elements or members, for example. These modifications would be apparent to those having ordinary skill in the art to which this invention relates and are intended to be within the scope of the claims which follow.

The invention claimed is:

1. A knee rail system supporting a load on a wearer, comprising:
a knee rail mechanism comprising:
a knee rail,
an attachment point connected to a calf beam; and
a knee joint attached to a thigh beam, and forming therethrough an aperture through which the knee rail extends, such that the knee joint is disposed on and slidingly engages the knee rail on an end of the knee rail mechanism opposite the attachment point.

2. The knee rail system of claim 1, wherein the knee rail system is configured to be positioned proximate to a knee of the wearer.

3. The knee rail system of claim 1, wherein when the wearer is standing straight and not moving, the thigh beam and the calf beam are aligned, and that the knee joint is positioned on the knee rail on a posterior side of the calf beam to support an applied force from the load.

4. The knee rail system of claim 1, wherein when the wearer's leg is lifted while in locomotion, the knee joint slides on the knee rail to a position on an anterior side of the calf beam.

5. The knee rail system of claim 1, wherein the knee rail is configured to be disposed at angle from 10 degrees to 80 degrees relative to a y-axis of the wearer.

6. The knee rail system of claim 1, further comprising a stopper configured to restrict the knee joint from bending.

\* \* \* \* \*